United States Patent

Hausheer et al.

[11] Patent Number: 5,910,491
[45] Date of Patent: Jun. 8, 1999

[54] HIGHLY LIPOPHILIC CAMPTOTHECIN DERIVATIVES

[75] Inventors: Frederick H. Hausheer, Boerne; Pavankumar N.V. Petluru, San Antonio; Dasharatha Reddy, San Antonio; Dhanabalan Murali, San Antonio; Kochat Haridas, San Antonio; Peddaiahgari Seetharamulu, San Antonio; Shijie Yao, San Antonio, all of Tex.

[73] Assignee: BioNumerik Pharmaceuticals, Inc., San Antonio, Tex.

[21] Appl. No.: 08/914,207

[22] Filed: Aug. 19, 1997

Related U.S. Application Data

[60] Provisional application No. 60/024,171, Aug. 19, 1996.
[51] Int. Cl.$^6$ .................................................. C07D 491/22
[52] U.S. Cl. .............................. 514/63; 514/283; 546/14; 546/48; 544/238
[58] Field of Search ................................. 546/14; 514/63

[56] References Cited

U.S. PATENT DOCUMENTS

| | | | |
|---|---|---|---|
| 3,894,029 | 7/1975 | Winterfeldt et al. | 546/48 |
| 4,545,880 | 10/1985 | Miyasaka | 204/157.71 |
| 5,004,758 | 4/1991 | Boehm et al. | 546/48 |
| 5,468,859 | 11/1995 | Fortunar et al. | 546/14 |
| 5,633,260 | 5/1997 | Hausheer et al. | 514/283 |

FOREIGN PATENT DOCUMENTS

| | | | |
|---|---|---|---|
| 2534601 | 2/1977 | Germany | 546/70 |

OTHER PUBLICATIONS

Sawada et al., Chem, Pharm. Bull, vol. 39, pp. 3183–8 (1991).

*Primary Examiner*—Donald G. Daus
*Attorney, Agent, or Firm*—Thomas J. Dodd

[57] ABSTRACT

Novel compounds, formulations and methods of treating patients with cancer are provided for in this invention. The compounds are derivatives of camptothecin, and specifically relate to compounds having novel substitutions at the C-7 position of the camptothecin scaffold B-ring. The formula I compounds are highly lipophilic, lactone stable, do not require metabolic activation, and are potent antineoplastic compounds.

14 Claims, No Drawings

HIGHLY LIPOPHILIC CAMPTOTHECIN DERIVATIVES

Provisional application No. 60/024,171, filed Aug. 19, 1996.

FIELD OF THE INVENTION

This invention relates to novel derivatives of camptothecin, and will have special application to derivatives having substitutions at the C-7 position on the B-ring of the camptothecin scaffold. The preferred substitutions include organic, inorganic, or combined organic/inorganic moieties.

BACKGROUND OF THE INVENTION

Camptothecin (CPT) and certain of its derivatives are potent antineoplastic agents that are currently the subject of numerous ongoing scientific investigations. Recently, the Untied States Food and Drug Administration approved the first two CPT derivatives (Irinotecan and Topotecan, discussed below) for human use as therapy for various forms of solid neoplasms.

Camptothecin was isolated in 1966 by Wall and Wani from *Camptotheca accuminata,* a Chinese yew. CPT was subsequently observed to have potent anti-cancer activity and was introduced into human clinical trials in the late 1970's. The closed E-ring lactone form of CPT was noted to be very poorly water soluble (approximately 0.1 microgram of drug dissolving in 1 mL of water). In order for CPT to be administered in human clinical trials it was first formulated with sodium hydroxide. This formulation resulted in hydrolysis of the lactone E-ring of the camptothecin molecule and formed the water soluble carboxylate species. The sodium hydroxide formulation of CPT created a water soluble CPT species that permitted clinicians to administer larger doses of the drug to cancer patients undergoing Phase I and Phase II clinical trials. It was not learned until much later that the carboxylate form of CPT had approximately one-tenth or less of the antitumor potency of the lactone form of CPT. Clinical trials with sodium hydroxide formulated CPT were disappointing due to the frequently observed significant systemic toxicities and the lack of antineoplastic activity, and clinical studies of CPT were halted in the early 1980's.

Further clinical development of CPT derivatives was not pursued until the mid-1980's. At that time it was reported that CPT had a unique mechanism of action involving the inhibition of DNA synthesis and DNA replication by interactions with the ubiquitous cellular enzyme Topoisomerase I (Topo I). This new information about the mechanism of action of CPT derivatives rekindled the interest in developing new Topo I inhibitors as antineoplastic drugs and subsequently several research groups began attempting to develop new CPT derivatives for cancer therapy. In general, it was observed that, like CPT, many of its derivatives were also very poorly soluble in water (less than 1 $\mu$g/mL). This low water solubility greatly limited the practical clinical utility of the drug because prohibitively large volumes, of fluid had to be administered to the patient in order to provide an effective dose of the drug. Because of the potent antineoplastic activity and poor water solubility of CPT and many of its derivatives in water, a great deal of research effort was directed at generating new CPT derivatives that were water soluble. This research is discussed below.

As stated earlier, CPT and many of its derivatives (Wall and Wani Camptothecin and Taxol:Discovery to Clinic-Thirteenth Bruce F. Cain Memoral Award Lecture Cancer Research 55:753–760; 1995) are poorly water soluble and are reportedly poorly soluble in a number of pharmaceutically acceptable organic solvents as well. There are numerous reports of newly created water soluble derivatives of CPT (Sawada, S. et al; Kingsbury, W. D. et al., Luzzio et al. Synthesis and Antitumor Activity of Novel Water Soluble Derivatives of Camptothecin as Specific Inhibitors of Topoisomerase I Jour. Med. Chem. 38:395–401; 1995) which have been synthesized in an attempt to overcome some of the significant technical problems in drug administration of poorly water soluble camptothecins to patients with cancer. Several water soluble CPT derivatives have been synthesized in an attempt to address the poor water solubility and difficulties in administration to patients. Well known examples of these water soluble CPT derivatives include: 9-dimethylaminomethyl-10-hydroxy camptothecin (Topotecan), 7-[(4-methylpiperazino)methyl]-10,11-ethylenedioxy camptothecin, 7-[(4-methylpiperazino)methyl]-10,11-methylenedioxy camptothecin, and 7-ethyl-10-[4-(1-piperidino)-1-piperidino]carbonyloxy camptothecin (Irinotecan or CPT-11).

Other substituted CPT derivatives with different solubility and pharmacologic properties have been synthesized as well; examples of these camptothecin derivatives include 9-amino camptothecin and 9-nitro camptothecin which are poorly soluble in both aqueous and nonaqueous media and have been tested in humans. 9-nitro camptothecin is a prodrug of 9-amino camptothecin and spontaneously converts to 9-amino camptothecin in aqueous media and in vivo in mice, dogs and humans (Hinz et al., Pharmacokinetics of the in vivo and in vitro Conversion of 9-Nitro-20(S)-camptothecin to 9-Amino-20 (S)-camptothecin in Humans, Dogs and Mice, Cancer Research 54:3096–3100; 1994).

The pharmacokinetic behavior of 9-nitro camptothecin and 9-amino camptothecin is similar to the water soluble camptothecin derivatives (Topotecan and Irinotecan) in that the plasma half lives are much shorter than the more lipid soluble CPT derivatives. Another major problem with 9-amino camptothecin is that its chemical synthesis using the semisynthetic method is carried out by nitration of CPT, followed by reduction to the amino group, which is a low yield synthesis. In addition, 9-amino camptothecin is light sensitive, heat sensitive and oxygen sensitive which renders the production and stabilization of 9-amino camptothecin difficult. The chemical decomposition reactions of 9-amino camptothecin can result in the formation of compounds that exhibit a large degree of toxicity in nude mice, whereas pure 9-amino camptothecin is significantly less toxic.

9-amino camptothecin is also difficult to administer to patients because it is poorly soluble in both aqueous and organic solvents. 9-nitro camptothecin is easier to produce and is more chemically stable, but with the chemical conversion to 9-amino camptothecin the drug is reportedly susceptible to MDR/MRP mediated drug resistance, which further limits its utility in the unfortunately common setting of drug resistant neoplasms. Based on pharmacokinetic behavior and chemical properties, 9-amino camptothecin is predicted to have reduced tissue penetration and retention relative to more lipid soluble camptothecin derivatives. Further, its poor solubility diminishes the amount of the drug which can cross the blood/brain barrier.

Of this diverse group of substituted CPT derivatives undergoing human clinical development, Irinotecan (CPT-11) has been one of the most extensively studied in Phase I and Phase II clinical trials in human patients with cancer. It is noteworthy that Irinotecan, which is a water soluble prodrug, is biologically inactive and requires activation by a putative carboxylesterase enzyme. The active species of Irinotecan is the depiperidenylated 10-hydroxy-7-ethyl camptothecin (claimed in Miyasaka et al. U.S. Pat. No. 4,473,692 (1984)), which is also known as SN38. SN38 is a toxic lipophilic metabolite which is formed by an in vivo bioactivation of Irinotecan by a putative carboxylesterase enzyme.

SN38 is very poorly soluble in water and has not been directly administered to human patients with cancer. Recently, it has been reported in human patients that SN38 undergoes further metabolism to form a glucuronide species which is an inactive form of the drug with respect to antitumor activity, and also appears to be involved in producing human toxicity (diarrhea, leukopenia) and substantial interpatient variability in drug levels of the free metabolite and its glucuronide.

Irinotecan has been tested in human clinical trials in the United States, Europe and Japan. Nearly 100 patient deaths directly attributable to Irinotecan drug toxicity have been reported in Japan alone. The Miyasaka et al. patents (U.S. Pat. Nos. 4,473,692 and 4,604,463) state that the object of their invention is to "provide 10-substituted camptothecins which are strong in anti-tumor activity and possess good absorbability in living bodies with very low toxicity" and "to provide new camptothecin derivatives which are strong in anti-tumor activity and possess good solubility in water and an extremely low toxicity".

Having multiple drug-related human deaths and serious patient toxicity, is clearly a failure of the Miyasaka et al. inventions to fulfill their stated objects. It is notable that tremendous interpatient variability with regard to drug levels of various forms, drug metabolism, certain pharmacokinetic properties and toxicity has been reported with the use of Irinotecan in human subjects with cancer. Parenteral administration of Irinotecan can achieve micromolar plasma concentrations of Irinotecan that, through metabolism to form SN38, can yield nanomolar concentrations of the active metabolite SN38. It has recently been reported in human subjects that SN38 undergoes further metabolism to form the SN38 glucuronide (Gupta et al. Metabolic Fate of Irinotecan in Humans: Correlation of Glucuronidation with Diarrhea. Cancer Research 54:3723–3725).

This further metabolic conversion of Irinotecan is important, since there is also reportedly large variability in the conversion of Irinotecan to SN38 and large interpatient variability in the metabolism of SN38 to form the inactive (and toxic) SN38 glucuronide in human subjects. (Gupta et al. Metabolic Fate of Irinotecan in Humans: Correlation of Glucuronidation with Diarrhea. Cancer Research 54:3723–3725; 1994 and Ohe, Y. et al., Phase I Study and Pharmacokinetics of CPT-ll with 5-Day Continuous Infusion. JNCI 84(12):972–974, 1992).

Since the amount of Irinotecan and SN38 metabolized is not predictable in individual patients, significant clinical limitations are posed and create the risk of life-threatening drug toxicity, and/or risk of drug inactivity due to five possible mechanisms: (1) conversion of greater amounts of Irinotecan to SN38; (2) inactivation of SN38 by glucuronidation; (3) conversion of SN38 glucuronide to free SN38; (4) lack of antineoplastic activity due to the conversion of lesser amounts of Irinotecan to form SN38; and (5) lack of antineoplastic activity by more rapid and extensive conversion of SN38 to form the glucuronide species. It is important to note that even a doubling of the plasma concentration of the potent Irinotecan metabolite SN38 may result in significant toxicity, because free SN38 exhibits antineoplastic activity at nanomolar concentrations.

Another source of interpatient variability and toxicity is the in vivo de-glucuronidation of SN38 and similar CPT derivatives to produce a free and active species of the drug. Deglucuronidation of a CPT derivative which is susceptible to A-ring glucuronidation, such as SN38, results in an increase in the plasma or local tissue concentration of the free and active form of the drug, and if high enough levels were reached, patient toxicity, and even death may result.

The present invention takes both glucuronide formation and deglucuronidation into account, since these compositions of matter will not undergo extracyclic A-ring or B-ring glucuronidation.

SUMMARY OF THE INVENTION

The compounds of the present invention have significant utility as highly efficacious antineoplastic drugs, and are significantly less toxic than the prior art CPT derivatives. The new compositions do not undergo A-ring or B-ring glucuronidation (and implicitly deglucuronidation), and they are not prodrugs requiring metabolic activation. Further, because the compounds of this invention are highly lipophilic, they can be administered directly in the active lactone form and will have superior bioavailability relative to water-soluble CPT derivatives.

The present invention is also aimed at overcoming other important limitations in bioavailability/pharmacokinetics and common tumor mediated drug resistance mechanisms observed with the use of water soluble camptothecins or 9-amino or 9-nitro substituted camptothecins as anticancer agents. This invention of new C-7 substituted CPT lactone compositions have greater clinical utility for treating patients with cancer based on several chemical and pharmacologic properties.

First, the direct administration of more lipid soluble camptothecins will result in clinical advantages over other CPT derivatives because of relatively superior tissue penetration, bioavailability and tissue retention. In many instances, it is more useful and convenient to administer the drug orally to cancer patients, and the superior lipid solubility and small molecular size of the CPT derivatives of this invention will have a great advantage over water soluble CPT derivatives in the setting of oral (and topical) administration.

The CPT derivatives disclosed and claimed in the present invention represent a new class of antineoplastic compounds that do not require metabolic activation and have exhibited potent antineoplastic activity against common types of cancer including but not limited to cancers of the lung, breast, prostate, pancreas, head and neck, ovary, melanoma and colon. The compounds described by the instant invention possess Topoisomerase I inhibitory activity similar to that of other CPT derivatives but have significant structural modifications rationally designed for superior active site binding capability and tissue penetration and avoid untoward metabolism and drug resistance mechanisms which are common in human and other mammalian neoplasms.

Until now, lipophilic CPT derivatives with poor water solubility have not been pursued because of limitations in pharmaceutical formulations and methods of use. These novel camptothecin compositions can be readily formulated in a pharmaceutically acceptable manner by dissolving the drug composition in an organic solvent or a mixture of organic solvents which have a high degree of physiologic safety, thus allowing the direct administration of these new classes of compounds as active species to cancer patients.

In view of very limited number of potentially active CPT derivatives in the poorly water soluble and highly lipid soluble category, there clearly remains a large unmet need to develop potent, new, poorly water soluble, highly lipophilic camptothecins which do not require metabolism to an active species and are less susceptible to metabolic inactivation and clinically important types of drug resistance. The new compounds disclosed and claimed in the present invention address these unmet needs.

The chemical modifications of the CPT scaffold to other derivatives can be broadly classified via total synthesis (Comins, D. et al. and Danishefsky, S. J et al and references cited therein) or by efficient semisynthetic approaches utilizing relatively inexpensive and readily available precursors.

The inventors have made a surprising discovery of several new chemical substitutions in the 20(S) CPT molecule (or 20(RS) CPT mixture) which possess the following characteristics:

1. Potent antitumor activity (nanomolar or subnanomolar activity in inhibiting the growth of human and animal tumor cells in vitro);
2. Potent inhibition of Topoisomerase I;
3. Lack of susceptibility to MDR/MRP drug resistance;
4. No metabolic drug activation required;
5. Lack of A-ring or B-ring glucuronidation;
6. Can be administered in the lactone species directly to patients for the purpose of treating a variety of neoplasms;
7. Small molecular weight (e.g., MW<600);
8. Highly soluble in organic pharmaceutical solvents or co-solvents (e.g., propylene glycol, PEG 300–400, dimethyl acetamide, dimethyl isosorbide, n-methyl pyrrolidinone); and
9. Can be administered orally, in addition to parenterally and topically, to subjects with cancer.

For the purpose of this invention it is also important to note that Miyasaka et al. (U.S. Pat. No. 4,399,282) state the following:

"As camptothecin itself carries a lactone ring as ring E, this lactone ring is opened by the action of an alkaline reagent, Similary, when the camptothecin derivatives of the present invention are treated, for example with an alkali metal hydroxide or carbonate in a conventional manner at room temperature or at an elevated temperature, the derivatives can be converted into corresponding alkali metal salt such as the sodium, potassium or lithium salt. These salts are all water-soluble and are of course involved in the scope of this invention. These salts are easily converted again into the free form by the action of an acid or in vivo. Thus, the pharmacological effect of the camptothecin derivatives is not influenced by such treatments. A preferable salt of the camptothecin derivative is the sodium or potassium salt."

The inventors submit that this teaching by Miyasaka et al. is incorrect with respect to CPT derivatives possessing an unmodified 20(S) E-ring lactone, since the pharmacological behavior and antineoplastic activity of the CPT derivatives will be profoundly and adversely influenced by such treatments as follows. By treating camptothecins with alkali metal hydroxides or carbonates, the CPT derivative will form the CPT carboxylate species by base-mediated hydrolysis of the E-ring lactone. The resulting CPT derivative carboxylate species will be water soluble and have substantially reduced antineoplastic activity and adversely altered pharmacokinetic and/or drug distribution behavior, and is not the preferred form of the drug. The inventors submit that the lactone E-ring species of CPT (and its derivatives) is the preferred form of the drug for administration to subjects with cancer.

Further, there will be a difference in the pharmacological properties and behavior of the intact lactone E-ring species versus the carboxylate species of camptothecin derivative in vivo in subjects. The carboxylate species of the camptothecin derivative has a significantly shorter plasma half life and exhibits greater toxicity than the lactone species. This is supported by pharmacologic evidence from clinical studies in humans and other mammalian species receiving sodium camptothecin, 9-amino camptothecin and Topotecan (Supko and Malspeis, Pharmacokinetics of the 9-amino and 10,11-Methylenedioxy Derivatives of Camptothecin in Mice, Cancer Research 53:3062–3069; 1993; Haas et al., Phase I/Pharmacokinetic Study of Topotecan by 24-Hour Continuous Infusion Weekly, Cancer Research 54:1220–1226; 1994).

Since water soluble forms of a drug do not penetrate lipid membranes of tissues as well as lipid soluble drugs, the carboxylate species of CPT derivatives are predicted to have lower bioavailability relative to CPT derivatives which have the lactone E-ring. Lower bioavailability of the drug will lead to a reduction in the effectiveness of treatment and may increase the risk of patient toxicity.

Since this invention teaches the objective of creating new and useful lipophilic, poorly water soluble CPT derivatives suitable for nonaqueous oral and parenteral formulations, from the standpoint of improving cancer therapy, this invention also teaches new convergent and efficient chemical syntheses of these novel substituted CPT derivatives using commercially available and relatively inexpensive natural isolates of CPT.

Accordingly, a number of new B-ring modifications are taught in this invention. More specifically, the C-7 position of the B-ring is one of the preferred sites of chemical modification using new chemical substituents which impart useful pharmacological, biological and chemical properties to these new compositions of matter.

Certain lipophilic substitutions at the C-7 position of CPT incorporate chemical groups via Minisci-type free radical alkylations on a protonated CPT or on modified substrates. Minisci-type regiospecific alkylations permit the creation of a one carbon less alkyl chain with respect to the starting aldehyde or alcohol or carboxylic acid. The reaction mechanism suggests that in the case of an aldehyde the introduction of the side chain occurs via an in situ decarbonylation to generate a one carbon less alkyl radical with concomitant evolution of carbon monoxide.

A limited number of acylated or functionally modified C-7 formyl derivatives are also reported but their synthesis has multi-step requirements. Other synthetic strategies aiming to anchor lipophilic moieties are rarely attempted. The reason why other possibilities are not attempted can be explained by limitations in the usage of poorly water soluble compounds or due to the fact that nitrogen containing heterocycles normally demand drastic reaction conditions for electrophilic substitutions such as Friedel Crafts alkylations or acylations and Vilsmier- Haack reactions.

The present invention teaches a novel process of regiospecific homolytic acylation of CPT and CPT derivatives at the C-7 position based on a Minisci-type reaction. A slight variation to the earlier stated methodology for C-7 alkylation permits the stabilization of the transient acyl radical that enables us to acylate the CPT skeleton in high yield. The present invention also describes novel processes to furnish certain key versatile synthons for making transformations at the C-7 position.

The invention also provides for pharmaceutical formulations of the new compounds, which formulations are pharmaceutically acceptable, safe for use with patients, and do not affect the efficacy of the active drug ingredient.

The invention also contemplates methods of treatment of several types of neoplasms. The methods all include the administration of an effective amount of one of the compounds of this invention to a patient suffering from one of the indicated diseases.

The compounds of this invention are of the formula:

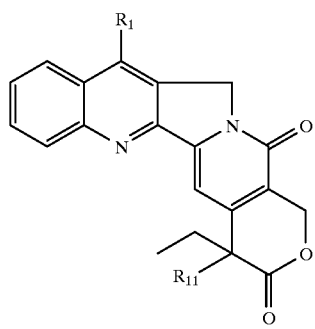

(I)

wherein $R_1$ is acyl; $C_2$–$C_8$ alkenyl or $C_2$–$C_8$ alkynyl optionally substituted by one or more halogen atoms or $OR_4$ or lower alkyl for a corresponding hydrogen atom therein;
halo; oxo; aryl optionally substituted by one or more halogen atoms; arylalkyl; arylalkenyl; arylalkynyl; heterocycle; $SR_5$; —S(O)-lower alkyl; —SO$_3$CF$_3$; -lower alkyl-P(O)$R_6R_7$; or —X—(C$_0$–C$_6$ alkyl, alkenyl, or alkynyl)—SiR$_8$R$_9$R$_{10}$;
$R_4$, $R_5$, $R_6$, $R_7$, $R_8$, $R_9$, and $R_{10}$ are each individually hydrogen or lower alkyl;
$R_{11}$ is hydrogen, hydroxy or acetoxy; and
X is sulfur or X is absent.

It is an object of the present invention to provide a fascile and extremely efficient synthetic methodology for the preparation of a new class of C-7 substituted camptothecins.

It is still another object of the present invention to provide a novel process for the preparation of 7-keto camptothecin (camptothecinone), 7-chloro and 7-bromo camptothecins as intermediates for the desired compositions.

Another object is to provide new and useful derivatives of CPT which are highly efficacious as antineoplastic agents.

Another object is to provide for new and useful methods of treating patients with various antineoplastic diseases.

Other objects will become apparent from a reading of the following specification and claims.

DESCRIPTION OF THE PREFERRED EMBODIMENT

Definitions

"Scaffold" means the fixed part of the molecule of the formula given.

"Fragments" are the variable parts of the molecule, designated in the formula by variable symbols, such as $R_x$ or the like. Fragments may include one or more of the following moieties:

"$C_x$–$C_y$" alkyl means a straight or branched-chain hydrocarbon containing as few as x and as many as y carbon atoms. Examples include "$C_1$–$C_6$ alkyl" (also referred to as "lower alkyl"), which includes a straight or branched chain hydrocarbon with no more than 6 total carbon atoms.

"$C_x$–$C_y$ alkenyl (and, similarly $C_x$–$C_y$ alkynyl)" means a straight or branched chain hydrocarbon with at least one double bond (alkenyl) or triple bond (alkynyl) between two of the carbon atoms.

"Halogen" or "Halo" means chloro, fluoro, bromo or iodo.

"Acyl" means —C(O)—X, where X is hydrogen, lower alkyl, aryl, lower alkenyl or lower alkynyl.

"Aryl" means an aromatic ring compound of one or more rings comprised entirely of carbon atoms.

"Arylalkyl" means an aromatic ring as defined above, bonded to the scaffold through an alkyl moiety (the attachment chain).

"Arylalkenyl" and "Arylalkynyl" mean the same as "Arylalkyl", but including one or more double or triple bonds in the attachment chain.

"Heterocycle" means a cyclic moiety of one or more rings, fused or unfused, wherein at least one atom of one of the rings is a non-carbon atom. Preferred heteroatoms include oxygen, nitrogen, sulfur and phosphorous, or any combination of two or more of those atoms.

Examples of the above moieties are as follows:

$C_1$–$C_6$ alkyl includes methyl, ethyl, propyl, isopropyl, butyl, isobutyl, sec-butyl, tert-butyl, pentyl, hexyl, amyl and the like;

$C_2$–$C_8$ alkenyl or alkynyl includes vinyl, propenyl, butenyl, acetylenyl, propynyl, and other like moieties with double and triple bonds;

Acyl includes formyl, acetyl, propionyl and others;

Aryl includes phenyl and naphthyl, as well as substituted variants wherein one of the hydrogen atoms bonded to the ring atom is substituted by a halogen atom, an alkyl group, or another of the above-listed moieties;

Arylalkyl includes benzyl, phenethyl, and the like;

Arylalkenyl and arylalkynyl includes phenyl vinyl, phenylpropenyl, phenylacetylenyl, phenylpropynyl and the like; and Heterocycle includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

The camptothecin derivatives of the present invention have the following general formula:

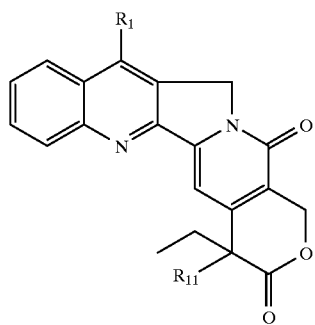

(I)

wherein $R_1$ is acyl; $C_2$–$C_8$ alkenyl or $C_2$–$C_8$ alkynyl optionally substituted by one or more halogen atoms or $OR_4$ or lower alkyl for a corresponding hydrogen atom therein; halo; oxo; aryl optionally substituted by one or more halogen atoms; arylalkyl; arylalkenyl; arylalkynyl;

heterocycle; $SR_5$; —S(O)-lower alkyl; —$SO_3CF_3$; -lower alkyl—P(O)$R_6R_7$; or —X—($C_0$–$C_6$ alkyl, alkenyl, or alkynyl)—$SiR_8R_9R_{10}$;

$R_4$, $R_5$, $R_6$, $R_7$, $R_8$, $R_9$, and $R_{10}$ are each individually hydrogen or lower alkyl;

$R_{11}$ is hydrogen, hydroxy or acetoxy; and

X is sulfur or X is absent.

Alkylation of protonated camptothecin

The homolytic alkylation of camptothecin is generalized for a variety of alkyl substitutions at the C-7 position. While designing these processes for scale-up synthesis, factors such as simplicity, economy and availability of certain reagents, overall yield and selectivity have been carefully considered. The Minisci type alkylation (Minisci, F., 1973) is also optimized for various phenolic camptothecins without prior protection to the phenolic moiety. Minisci type alkylations of heteroaromatic bases have several advantages. Polar effects related to the nucleophilic character of the carbon-centered radicals and the electron deficiency of the protonated heterocyclic bases play a significant role in the synthetic yield of these reactions.

Reactivity and positional and substrate selectivity are two of the major merits (Vorbruggen, H., 1988). The rearomatization of the radical adduct is very selective and quick due to strongly nucleophilic radicals of the pyridinyl type. Reactions of this category are an Iron (II) salt mediated exothermic process that affords selective substitutions at α or γ positions of the heterocyclic ring. In the present invention, we have taken advantage of these factors to selectively introduce alkyl substitutions at the C-7 position of camptothecin skeleton such as certain novel lower alkyl groups, trifluoroethyl, polyfluoroethyl and monofluoro ethyl groups.

C-7 Acylation of protonated camptothecin

Acylation of the heteroaromatic bases such as camptothecins are of great interest due to the fact that electrophilic aromatic substitutions are generally ineffective with these types of heterocyclic systems. Further, the high reactivity and selectivity of the C-7 position of camptothecin due to increased nucleophilicity under acidic conditions would provide the desired products with minimal unwanted by-products. The respective acyl radicals without the elimination of a $C_1$ unit can be best obtained from the corresponding aldehydes in the presence of excess trifluoro acetic acid at low temperature. Minisci type alkylation procedures were found extremely effective with various camptothecin derivatives. However, such alkylations conventionally install a carbon chain or unit that is one carbon less than the starting material. The present invention teaches a modified Minisci type reaction that permits the desired homolytic carbon chain generation as a determinant based up on the type of aldehyde used in the reaction medium. These types of homolytic substitutions are widely accepted as an alternate tool for heterocyclic systems where classical Friedel-Crafts reactions can not be effectively performed. In principle, the more stable the carbonium ion is the more nucleophilic will be the corresponding radical.

Therefore, almost all the electrophilic species that are useful in the Friedel-Craft reaction can be utilized, as the corresponding radicals, for the selective substitution of the heteroaromatic bases. This opens a wide variety of organic compounds as radical sources for C-7 substitution of camptothecin. Those types of compounds include: alkanes, alkenes, alkylbenzenes, alkyl halides, alcohols, ethers, aldehydes, ketones, carboxylic acids, amines, amides, oxaziridines, N-chloramines etc. The major determinants of the reaction conditions that lead to either the desired alkylated product or acylated product are largely controlled by the type of acid present in excess and the free radical initiator.

C-7 Halogenation

Chlorination and bromination at the C-7 position of camptothecin are best done on an electron deficient nitrogen bearing camptothecin skeleton. It is evident from the literature that the oxide function at $N^1$ position of a quinoline moiety could generate substantial nucleophilicity to the α and γ positions of the heterocylic base. Such effects would be enhanced further upon a protonation event on the N-1 oxide. In the case of the camptothecin scaffold, an absolute γ selectivity is envisioned as the a positions are already blocked. The inventors' observed that such nucleophilic halogenation proceeds smoothly and selectively on 20-acetoxy-camptothecin-1-oxide in presence of excess trihalophosphine oxide at 40° C. The camptothecin derivatives thus prepared are subsequently utilized as synthons for cross-coupling reactions as stated below.

Stille type coupling at the C-7 position

Stille's procedure (J. K. Stille, 1986; J. K. Stille 1987) provides one of the most useful methods to construct carbon-carbon bonds. The reaction is catalyzed by organometallic reagents derived from group IA metals via coupling of organic electrophiles and organostannanes in presence of lithium halide.

Similar cross coupling where boronic acids or esters are employed in place of organostannanes are called Suzuki cross-coupling Reaction (George B. S., 1994). Excess stoichiometric amounts of lithium chloride are essential for the completion of the reaction as lithium chloride is consumed for the formation of tributyltin chloride and lithium triflate. A variety of organic electrophiles are used in the cross-coupling reaction of which bromides, iodides and triflates are extensively studied (Kurt Ritter, 1993). The rate of the reaction can be modulated readily based on the composition and concentration of the organic electrophile. A better understanding of the mechanistic aspects of the rate limiting transmetallation process led to the recent developments involve the use of cocatalytic Cu(I) and Pd(O) species in this coupling reaction. The role of the Cu(I) species has been envisioned (Liebeskind, 1990) in Sn/Cu transmetallation.

The resulting organocopper species would then transmetallate onto Pd(II) at a higher rate than the stannane itself. This is currently known as the "copper effect." The scope of the reaction is extremely wider than this application. A large number of structurally varied organic groups including vinyl, alkyl, allyl, aryl, acetylenic, amino, and amido moieties on tin could easily be transferred onto aryl and heteroaryl skeletons displacing the vinyl triflate or unsaturated halides in high yields. However, the conventional Stille reaction conditions are unacceptable for some of our novel entities. Further, modifications were sought out in this direction that resulted in making the palladium catalyzed cross-coupling highly conceivable to incorporate such fuctionalities in extremely mild conditions as well as in high yields. In all these coupling reactions, tris (dibenzylideneacetonyl)bis palladium(O) served as the catalyst while tri(2-furyl)phosphine exhibited its noticeable role in enhancing the rate of activation of the ligand properties even at room temperature.

Suzuki Cross-Coupling Reaction

The Stille coupling and the Suzuki coupling are very similar in many respects at a fundamental level, however, in terms of scalability for large scale production of the new compositions the Suzuki coupling has certain advantages. The necessary use of tin in stoichiometric amounts in the Stille reaction makes the Suzuki coupling more attractive. However, no generally applicable set of reaction conditions has yet been found to affect this reaction. At the same time, Suzuki coupling is an extremely convergent approach for the incorporation of cyclopropyl, phenyl and certain other polyfluoroalkyl functionalities into a camptothecin scaffold. Recent reports by Wright and co-workers (Wright, S. W., 1994) simplified the reaction conditions by employing fluoride ion instead of incompatible bases to generate boronate anion. However, boronate anion may be crucial in the reaction medium to effect boron to palladium transmetallation. The recent report unambiguously suggested the capability of fluoride ions to exhibit significant affinity for boron and considerable stability of fluoborate ions. Additionally, the report also has addressed the favoring weak basicity and poor nucleophilicity of fluoride ions and the weakness of the palladium-fluorine bond in Suzuki coupling reactions.

Pyridone Chemistry

Effective functionalization of the pyridone moiety generated with in the camptothecin scaffold is effectively translated to prepare C-7 substituted camptothecin derivatives as highly lipophilic camptothecin analogs. The camptothecinone is thus utilized as a versatile synthon for preparing the key C-7 triflyloxy derivative. Regiospecificity at the γ position is easily accomplished in the case of camptothecin series as the a position is already a part of the ring structure. The in situ generated trimethylsulfonyl enolate is conveniently hydrolyzed into the desired keto moiety in presence of water. This C-7 keto intermediate upon treatment with dimethylsulfate and potassium carbonate yielded the 7-methoxy camptothecin. The keto compound is converted to respective 7-triflate by treating with triflic anhydride in the presence of a suitable organic base under anhydrous reaction conditions.

C-7 Trifluoromethane sulfonyloxy-20 acetoxy camptothecin as a pivotal intermediate The excellent leaving group properties of trifluoromethane sulfonate persuaded the inventors to incorporate such a group at C-7 and explore the versatile applicability to displace with the novel entities of this invention at extremely mild reaction conditions. As a preferred embodiment of the present invention, a broad utility of C-7 camptothecin triflate is described in order to incorporate novel entities such as cross-coupled carbon bearing moieties, vinyl substituents, acetylenic substituents, thioethers of pharmacological significance and also as a precursor for organocuprate addition at the C-7 position, permitting the incorporation of significantly bulky substituents such as trimethyl silyl. The pharmacological importance of trimethylsilyl, in particular towards drug delivery mechanisms, is still an area with tremendous exploratory significance. The present invention clearly teaches the potentiating characteristics of the trimethylsilyl moiety.

C-7 Silylation

An efficient alkali metal such as lithium or potassium assisted alkylation or heteroatom incorporation strategy or organometallic mediated alkylation or heteroatom incorporation on camptothecin has not yet been successfully accomplished due to the extreme sensitiveness of C-5 benzylic protons and the E-ring methylene protons associated with the lactone moiety. Conventional alkylation procedures suffer from the severe disadvantages that at least these two acidic sites of the molecule would be attacked by equivalence of the base. In view of these aspects, a persistent effort to circumvent these problems have been sought out. Several palladium mediated cross-coupling reactions were attempted with no success. The failure to provide the desired product via organopalladium intermediate suggested us the steric hindrance of significantly bulkier trimethylsilyl group at C-7. In addition, several Minisci type reactions generated in situ free radical alkylation at the electron deficient C-7 position. During our investigative efforts, we invented the following highly efficient methodology.

As a preferred embodiment of this invention, we would like to teach an elegant organocuprate mediated displacement of C-7 triflate moiety with trimethylsilyl group. The organocopper conjugate, analogous to Noyori's method, derived from cuprous iodide, n-butyl phosphine and trimethylsilyl lithium illustrated its versatility to displace the C-7 triflate preferentially without interfering with the C-5 benzylic protons or C-17 methylene protons at low temperature. The trimethylsilyl anion is conveniently generated from hexamethyl disilane in presence of a suitable organic base at low temperature.

On the other hand incorporation of the ethyl trimethylsilyl group at C-7 is accomplished via Minisci type alkylation. The key silyl synthon is prepared from the trimethylsilyl propanol. The alcohol is oxidized into corresponding aldehyde using pyridinium chlorochromate in methylene chloride at room temperature. The aldehyde thus obtained is then fractionated to remove the self condensed aldol products. The Minisci type alkylation is performed on camptothecin thereby the overall synthetic approach could be reduced to a single step process.

The following Schemes illustrate the general processes used to produce novel camptothecin derivatives of this invention, and in no way are to be considered limiting of the invention.

Scheme I

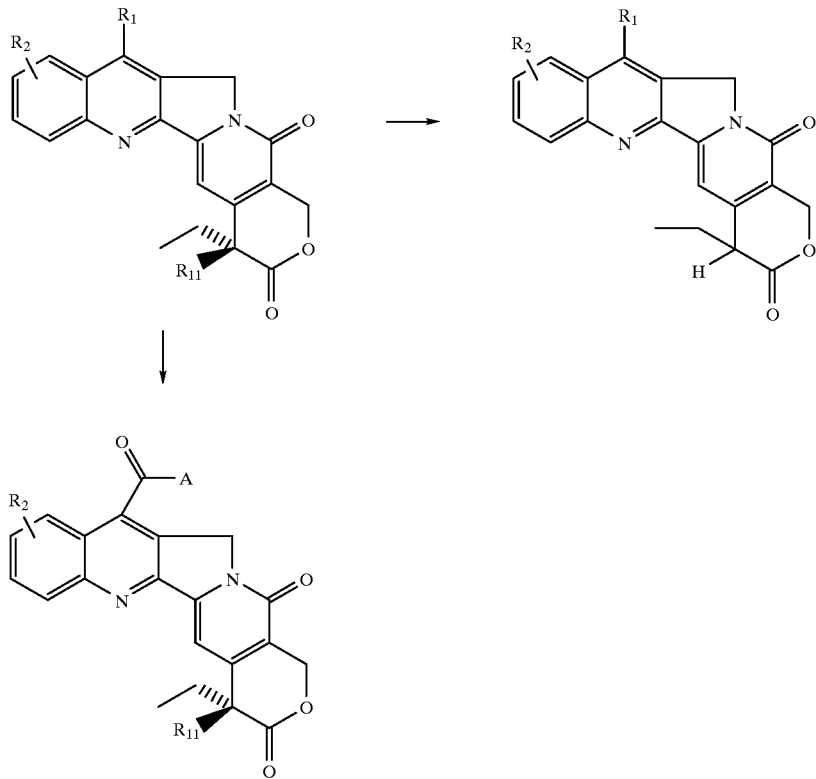

Scheme I illustrates the preparation of the C7-acyl derivatives of this invention, and also the preparation of the 20-dehydroxy derivative of CPT.

The selective acylation at the C7-position on the B-ring is achieved by the procedures outlined above. In the above scheme, "A" represents an alky chain of 1–6 Carbon atoms, most preferably 1–2 Carbon atoms, to form 7-Acetyl CPT or 7-Propionyl CPT, and $R_{11}$ is hydroxy.

Conversion of the 20-hydroxy moiety to a hydrogen atom is achieved by a selective C-20 dehydroxylation. The novel dehydroxylation is accomplished by employing the versatility of Lawsson's Reagent or more gently by converting the 20-hydroxyl moiety into a better leaving group, preferably a trimethanesulfonyloxy block followed by reductive cleavage using a respective stannyl hydride.

Scheme II

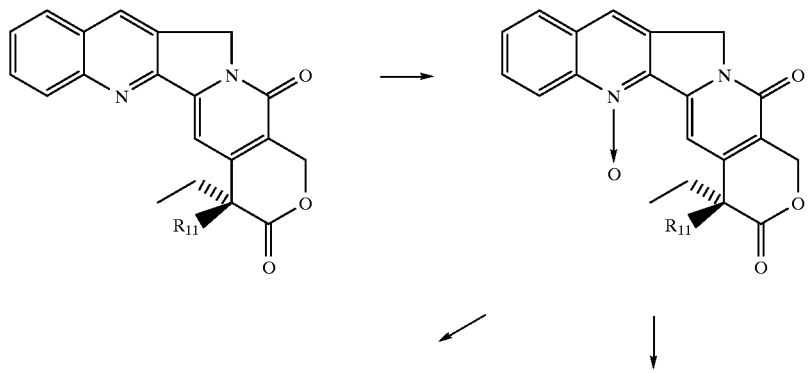

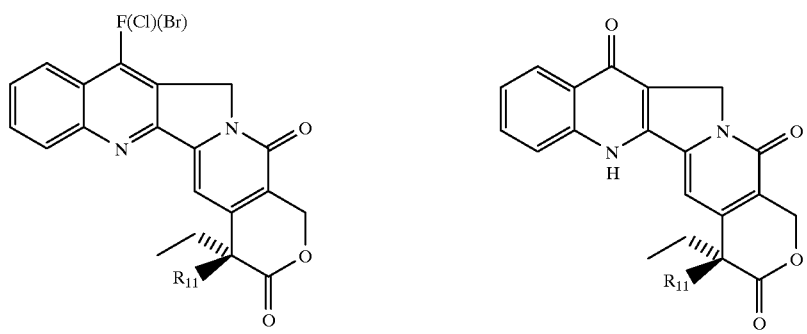

Scheme II illustrates the preparation of 7-halo CPT, and also the preparation of the key intermediate 7-keto CPT. The first step in the synthesis of either of these compounds is the conversion of CPT to camptothecin-1-oxide. In Scheme II, $R_{11}$ is typically a protected hydroxy moiety, most preferably an acetoxy moiety, which is converted to hydroxy after the 7-position moieties have been added. Typical deprotection of the 20-acetoxy moiety and conversion to 20-hydroxy is accomplished by use of alkali metal salts and alcohols, most preferably potassium carbonate and methanol.

The halogenation at C-7 is achieved by the general procedures described above. Conversion and regioselectivity of CPT-1-oxide to 7-keto CPT is also described above, with the most preferred procedures outlined in Example 3 below. 7-Keto CPT is used extensively as a key intermediate in many of the selective schemes for producing the 7-substituted CPT derivatives of this invention. Schemes III and IV detail the synthetic procedures for making the novel CPT derivatives which form the subject matter of this invention.

Scheme III illustrates the synthesis of the 7-trifluoromethanesulfonyloxy intermediate which is key to the substitution of the various 7-position moieties which form the subject matter of this invention.

As shown, 7-keto CPT is converted into this intermediate by reacting with a sulfate ester and an alkali metal salt, then with triflic anhydride (hexafluorodimethyl ether). The resulting 7-triflate intermediate possesses excellent properties for substitution reactions to be performed on the molecule, allowing for diverse moieties to be attached to the CPT scaffold.

Scheme III

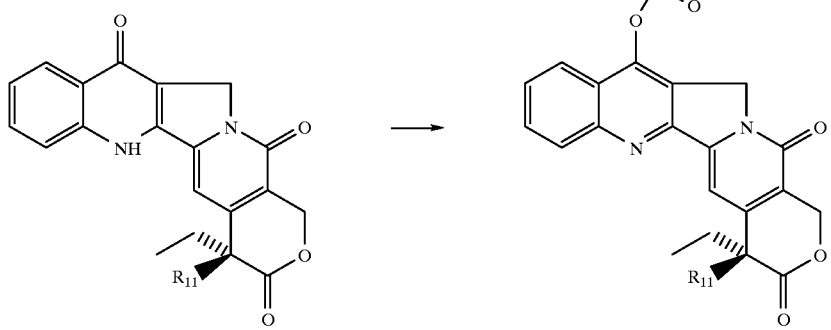

Scheme IV

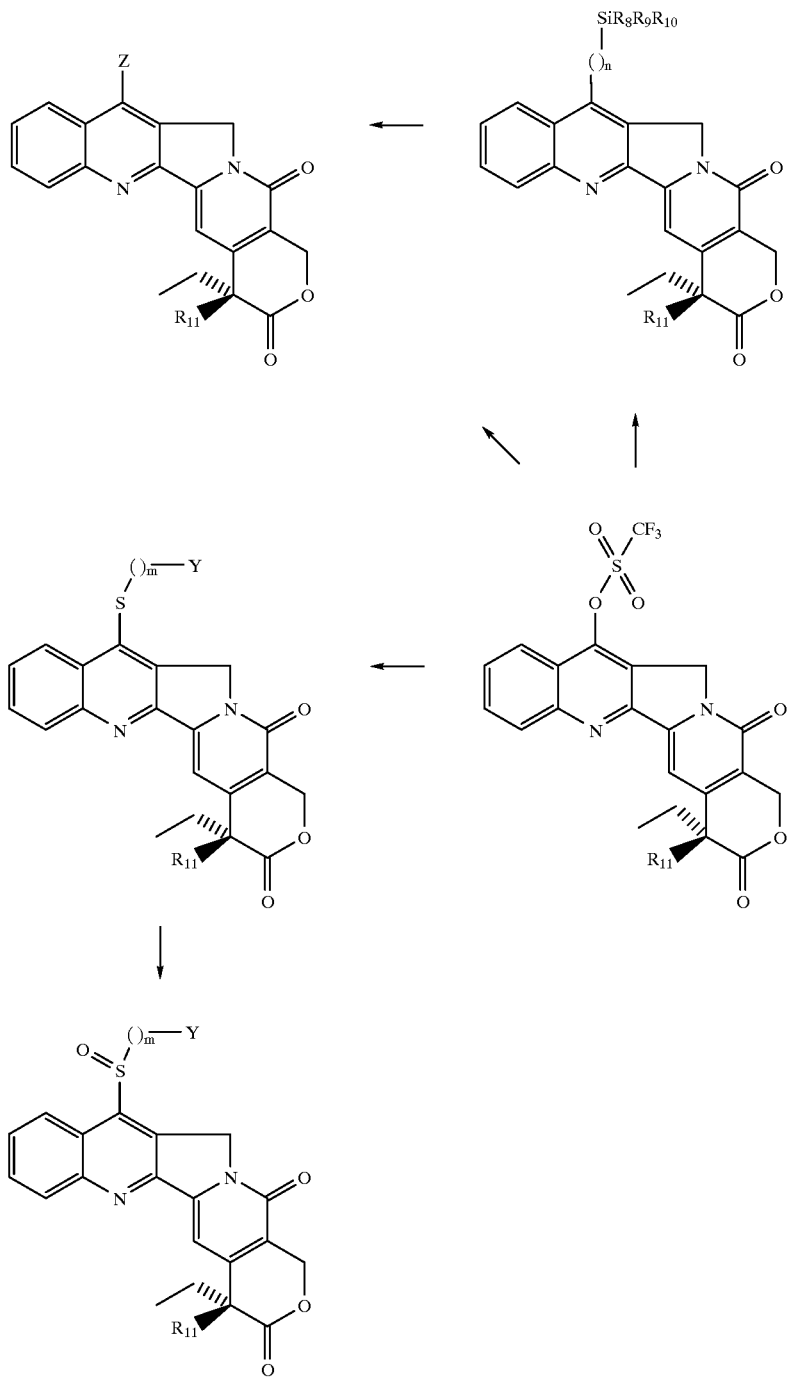

Scheme IV illustrates the synthesis of the novel C7-substituted CPT derivatives of this invention. The key intermediate, 7-trifluoromethanesulfonyl CPT, is converted into one of the novel compounds of this invention by following the general methods outlined in the specification, supra.

The two general moieties which are substituted directly for the triflyloxy moiety are the silyl moieties and the thioether moieties shown in scheme IV. As stated above, the silyl moieties are formed through a modified Stille coupling, through the use of a palladium mediated tributyltin-alkylsilane substitution. The $(\ )_n$—refers to an alkyl (or alkenyl or alkynyl) group, where n stands for the number of carbon atoms, preferably 0 to 6, most preferably 0 to 3. When n is 0, the preferred synthesis utilizes an organo-lithium mediated displacement using hexamethyl disilane as the preferred reagent.

The silyl moieties may be converted into 7-alkenyl or 7-alkynyl moieties (designated by the letter "Z"), by reacting with an alkali metal salt, which both removes the silyl moiety and also serves to convert the 20-acetoxy moiety to hydroxy. 7-alkenyl and 7-alkynyl substituted CPT derivatives may also be prepared directly from the 7-triflate by the modified Stille coupling as described above.

7-thioethers are prepared by reacting the 7-triflate with the appropriate alkyl sulfide under basic conditions. In the scheme shown ( )$_m$—stands for an alkyl (or alkenyl or alkynyl) group and m is 0 to 6, preferably 1 to 3. Y indicates that a silyl moiety may be appended to the terminal end of the reagent, and will be transferred to the resulting compound. An example of such a thioether reagent is 1-trimethylsilyl-2-mercapto ethane, which would form 7-($\beta$-trimethylsilyl)ethylthio CPT.

7-thioethers may be converted into the 7-sulfinyl derivatives by reacting with a peracid, such as perbenzoic acid, most preferably m-chloroperbenzoic acid. Other derivatives may be prepared by utilizing the syntheses described above, in conjunction with the specific examples listed below.

Specific Examples

The following examples illustrate selected modes for carrying out the invention and are not to be constructed as limiting the specification and claims in any way.

EXAMPLE 1

7-Acetyl Camptothecin

Camptothecin (5 g, 14.36 mmols) was dissolved in trifluoroacetic acid: acetic acid (60 mL; ratio, 1:1) and added deionized water (15 mL) and freshly distilled acetaldehyde (20 mL; excess) followed by dropwise addition of concentrated sulfuric acid (5 mL) at 0° C. using an ice bath over a period of 15 min. To the above stirred reaction medium is then introduced 70% aqueous solution of t-butylhydroperoxide (3 mL) followed by iron sulfate heptahydrate (7.8 g, 28 mmol) in 1 mL water. The reaction mixture was then stirred at 0° C. to 25° C. for an additional 24 hours. The reaction mixture was then diluted with water and extracted with diethyl ether (500 mL×1), chloroform (250 mL×1) and then using n-butanol (250 mL×4). The organic portions were extracted out using diethyl ether and chloroform and discarded as fractions lacking desired product, while the n-butanol portion was concentrated to dryness at 40° C. and the crude product was recrystallized from a 90% chloroform-methanol mixture to furnish 4.2 gm of the title compound (75% yield).

$^1$H NMR (300 MHz; d6-DMSO): 0.87 $\delta$ (3H, t, J=7 Hz); 1.86 $\delta$ (2H, q, J=5 Hz); 2.78 $\delta$ (3H, s); 5.29 $\delta$ (2H, m); 5.38 $\delta$ (2H, m); 6.51 $\delta$ (1H, bs, OH); 7.35 $\delta$ (2H, s); 7.78 $\delta$ (1H, t, J=13.5 Hz); 7.92 $\delta$ (1H, t, J=7.64 Hz); 8.13 $\delta$ (1H, d, J=8.35 Hz); 8.23 d (1H, d, J=8.38 Hz)

$^{13}$C NMR: $\delta$ 7.84, 30.41, 31.7, 50.27, 65.35, 73.21, 97.42, 119.78, 123.26, 124.86, 126.12, 131. 4, 138.5, 143.87, 143.25, 145.31, 149.34, 150.05, 156.63, 157.68, 172.46, 205.05

FAB-MS: 391 (M+1)

EXAMPLE 2

7-Propionyl Camptothecin

Camptothecin (1 g, 2.8 mmols) was dissolved in trifluoroacetic acid-acetic acid (6 mL; ratio, 1:1) and added deionized water (3 mL) and freshly distilled propionaldehyde (3.0 mL; excess) followed by dropwise addition of concentrated sulfuric acid (1 mL) at 0° C. using an ice bath during 15 min. To the above stirred reaction medium was then introduced a 70% aqueous solution of t-butylhydroperoxide (3 mL) followed by iron sulfate heptahydrate (1.56 g, 5.6 mmol) in 1 mL water. The reaction mixture was then stirred at 0° C. to 25° C. for an additional 24 hours. The reaction mixture was then diluted with water and extracted with diethyl ether (100 mL×1), chloroform (50 mL×1) and then using n- butanol (100 mL×4). The organic portions extracted out using diethyl ether and chloroform were discarded as fractions lacking desired product, while the n-butanol portion was concentrated to dryness at 40° C. and the crude product was recrystallized from a 90% chloroform-methanol mixture to furnish 0.86 gm of the title compound (74% yield).

$^1$H NMR (300 MHz; d6-DMSO): 0.87 d (3H, t, J=7 Hz); 1.26 $\delta$ (3H, t, J=6.8 Hz); 1.84 d (2H, q, J=5 Hz); 3.15 d (2H, q, J=5.1 Hz); 5.29 $\delta$ (2H, m); 5.38 $\delta$ (2H, m); 6.51 $\delta$ (1H, bs); 7.35 $\delta$ (2H, s); 7.72 $\delta$ (1H, t, J=13.5 Hz); 7.90 $\delta$ (1H, t, J=7.64 Hz); 7.98 $\delta$ (1H, d, J=8.35 Hz); 8.20 $\delta$ (1H, d, J=8.38 Hz)

$^{13}$C NMR: $\delta$ 7.54, 7.74, 30.31, 36.7, 49.81, 65.21, 72.33, 96.88, 119.48, 123.12, 125.69, 130.63, 131.72, 140.97, 143.14, 143.25, 145.31, 149.97, 156.55, 157.68, 172.36, 204.91

FAB-MS: 405 (M+1)

EXAMPLE 3

7-Keto camptothecin (Camptothecinone)

Camptothecin 1-oxide (1 gm, 2.7 mmol) was dissolved in trifluoroacetic acid (2 mL) and anhydrous methylene chloride (15 mL) and added trifluoroacetic anhydride (16 mL). The reaction mixture was then refluxed under a positive pressure of argon for 48 hours. The reaction mixture was then cooled to room temperature and diluted with water (15 mL) and stirred for 6 hours. The product was then precipitated out by pouring the reaction mixture into crushed ice. The precipitated product was then filtered, washed with excess water, once with diethyl ether and dried under vacuum to obtain 687 mg of the desired product (66% yield).

$^1$H NMR (300 MHz; d6-DMSO): 0.87 $\delta$ (3H, t, J=7 Hz); 1.96 $\delta$ (2H, q, J=5 Hz); 2.78 $\delta$ (3H, s); 5.86 $\delta$ (2H, m); 5.40 $\delta$ (2H, m); 6.81 $\delta$ (1H, bs); 7.38 $\delta$ (1H, t, J=13.5 Hz); 7.47 $\delta$ (2H, s); 7.71 $\delta$ (1H, t, J=7.64 Hz); 7.73 $\delta$ (1H, d, J=8.35 Hz); 8.14 $\delta$ (1H, d, J=8.38 Hz)

$^{13}$C NMR: $\delta$ 6.89, 29.55, 49.6, 66.123, 79.90, 94.78, 105.12, 118.48, 123.31, 124.26, 124.95, 132.06, 141.69, 143.55, 155.35, 164.88, 200.432

FAB-MS: 461 (M+1 for the triflic acid salt)

EXAMPLE 4

7-Trifluoromethanesulfonyloxy-20-acetoxy camptothecin

20-Acetoxy camptothecinone (220 mg, 0.54 mmols) was dissolved in anhydrous pyridine (4 mL) and anhydrous methylene chloride (10 mL). The above solution was stirred well while lowering the temperature to −10° C. using an ice bath. To it was then slowly introduced triflic anhydride (0.5 mL, 1.05 mol) and the reaction continued to completion. The reaction mixture was then diluted with methylene chloride (20 mL), water washed and the organic portion was concentrated to dryness. The product thus obtained upon analysis was found substantially pure for the subsequent step.

$^1$H NMR (300 MHz; CDCl$_3$): 0.87 δ (3H, t, J=5.4 Hz); 2.12 δ (2H, q, J=7.2 Hz); 2.21 δ (3H, s); 5.42 δ (2H, ABq, J$^1$=17.5 Hz; J$^2$=6.1 Hz); 5.49 δ (2H, q, J=2.5 Hz); 7.14 δ (1H, s); 7.97 δ (1H, t, J=7.2 Hz); 8.05 δ (1H, t, J=7.9 Hz); 8.12 δ (1H, d, J=8.4 Hz); 8.35 δ (1H, d, J=6.2 Hz)

FAB-MS: 540 (M+1)

EXAMPLE 5

20-Acetoxy-7-chloro camptothecin

20-Acetoxy camptothecin-1-oxide (800 mg, 1.96 mmols) was taken up as a suspension in phosphorus oxychloride (10 mL) and stirred at 40° C. for 48 hours under a positive blanket of inert gas. The reaction mixture was then diluted with methylene chloride (25 mL) and cooled down to 0° C. using an ice bath. The reaction mixture was then diluted with water (50 mL) and stirred for 3 hours. The organic portion was then extracted out using methylene chloride (50 mL×5), concentrated and flashed through a bed of silica gel using chloroform to obtain the desired product (642 mg; 77.1%)

$^1$H NMR (300 MHz; CDCl$_3$): 0.90 δ (3H, t, J=5.4 Hz); 2.12 δ (2H, q, J=7.2 Hz); 2.21 δ (3H, s); 5.42 δ (2H, ABq, J$^1$=17.5 Hz; J$^2$=6.1 Hz); 5.49 δ (2H, q, J=2.5 Hz); 7.07 δ (1H, s); 7.87 δ (1H, t, J=7.2 Hz); 7.95 δ (1H, t, J=7.9 Hz); 8.21 δ (1H, d, J=8.4 Hz); 8.27 δ (1H, d, J=6.2 Hz)

FAB-MS: 425.1 (M+1)

EXAMPLE 6

7-Chloro camptothecin

20-Acetoxy-7-chloro camptothecin (100 mg, 0.23 mmols) was dissolved in reagent grade methanol (20 mL) and added aqueous potassium carbonate (20 mg in 5 mL water) and stirred for 1 hour at room temperature. The resulting reaction mixture was concentrated to 5 mL under vacuum and diluted with water (20 mL). The precipitated product was then filtered, dried and analyzed to the desired product (60 mg; 67%).

$^1$H NMR (300 MHz; CDCl$_3$): 0.87 δ (3H, t, J=5.4 Hz); 1.85 δ (2H, q, J=7.2 Hz); 3.6 δ (1H, s); 5.31 δ (2H, s); 5.43 δ (2H, s); 7.07 δ (1H, s); 7.87 δ (1H, t, J=7.2 Hz); 7.95 δ (1H, t, J=7.9 Hz); 8.21 δ (1H, d, J=8.4 Hz); 8.27 δ (1H, d, J=6.2 Hz)

$^{13}$C NMR: δ 7.54, 30.31, 49.81, 65.21, 72.33, 96.88, 119.48, 123.12, 125.69, 126.96, 130.63, 131.72, 140.97, 143.14, 143.25, 145.31, 149.97, 156.55, 157.68, 172.36

FAB-MS: 383.1 (M+1)

EXAMPLE 7

20-Acetoxy-7-vinyl-camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol) followed by tri(2-furyl)phosphine (20 mg, 0.074 mmol). The resulting solution was stirred for approximately 30 minutes at room temperature. Then added vinyl tributyltin (60 mL, 0.223 mmol). The reaction mixture was then stirred at room temperature for 48 hours. The resulting dark brown colored reaction mixture was then diluted with methylene chloride (25 mL), filtered, washed with water (15 mL). The crude product obtained after concentration was then flashed through a columnar bed of florisil, the fractions pooled, concentrated, dried under vacuum and analyzed.

$^1$H NMR (300 MHz; CDCl$_3$): 0.87 δ (3H, t, J=5.4 Hz); 1.85 δ (2H, q, J=7.2 Hz); 2.31 δ (3H, s); 3.6 δ (1H, s); 5.42 δ (2H, ABq, J$^1$=17.5 Hz; J$^2$=6.1 Hz); 5.61 δ (2H, s); 6.15 δ (2H, dd, J=12.8 Hz); 6.4 δ (1H, d, J=2.5 Hz); 7.07 δ (1H, s); 7.87 δ (1H, t, J=7.2 Hz); 7.95 δ (1H, t, J=7.9 Hz); 8.21 δ (1H, d, J=8.4 Hz); 8.27 δ (1H, d, J=6.2 Hz)

EXAMPLE 8

7-Vinyl camptothecin

20-Acetoxy-7-vinyl camptothecin (100 mg, 0.23 mmols) was dissolved in reagent grade methanol (20 mL) and added aqueous potassium carbonate (20 mg in 5 mL water) and stirred for 2 hours at low temperature. The resulting reaction mixture was acidified to pH 4 using 1N HCl and the precipitated product was filtered, dried and analyzed to the desired product (30 mg; 47%).

$^1$H NMR (300 MHz; CDCl$_3$): 0.87 δ (3H, t, J=5.4 Hz); 1.85 δ (2H, q, J=7.2 Hz); 3.6 δ (1H, s); 3.6 δ (1H, s); 5.42 δ (2H, ABq, J$^1$=17.5 Hz; J$^2$=6.1 Hz); 5.61 δ (2H, m); 6.15 δ (2H, dd, J=12.8 Hz); 6.4 δ (1H, d, J=2.5 Hz); 7.07 δ (1H, s); 7.87 δ (1H, t, J=7.2 Hz); 7.95 δ (1H, t, J=7.9 Hz ; 8.21 δ (1H, d, J=8.4 Hz); 8.27 δ (1H, d, J=6.2 Hz)

$^{13}$C NMR: δ 7.54, 30.31, 49.81, 65.21, 72.33, 96.88, 99.6, 119.48, 123.12, 125.69, 126.96, 130.63, 131.72, 137.2, 140.97, 143.14, 143.25, 145.31, 149.97, 156.55, 157.68, 172.36

FAB-MS: 373(M+1)

EXAMPLE 9

20-Acetoxy-7-(γ-trimethylsilyl)propyn-2-yl camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol), diisopropyl ethylamine (50 μL) followed by tri (2-furyl)phosphine (20 mg, 0.074 mmol). The resulting solution was stirred for approximately 30 minutes at room temperature. Then added propargylic trimethylsilane (0.1 mL). The reaction mixture was then stirred at room temperature for 48 hours. The resulting dark brown colored reaction mixture was then diluted with methylene chloride (25 mL), filtered, washed with water (15 mL). The crude product obtained after concentration is then flashed through a columnar bed of florisil, the fractions pooled, concentrated, dried under vacuum and analyzed.

$^1$H NMR (300 MHz; CDCl$_3$): 0.38 δ (9H, s); 0.87 δ (3H, t, J=5.4 Hz); 2.3 δ (2H, q, J=7.2 Hz); 2.31 δ (3H, s); 5.42 δ (2H, ABq, J$^1$=17.5 Hz; J$^2$=6.1 Hz); 5.61 δ (2H, m); 7.07 δ (1H, s); 7.87 δ (1H, t, J=7.2 Hz); 7.95 δ (1H, t, J=7.9 Hz); 8.21 δ (1H, d, J=8.4 Hz); 8.27 δ (1H, d, J=6.2 Hz)

EXAMPLE 10

20-Acetoxy-7-(methyl)thio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 moles) and slowly bubbled methanethiol for 5 minutes and then the reaction mixture was stirred under a balloon pressure for 15 hours. After 15 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.

$^1$H NMR (300 MHz; CDCl$_3$): 0.87 δ (3H, t, J=5.4 Hz); 2.31 δ (2H, q, J=7.2 Hz); 2.28 δ (3H, s); 2.31 δ (3H, s); 5.42 δ (2H, ABq, J$^1$=17.5 Hz; J$^2$=6.1 Hz); 5.61 δ (2H, m); 7.07 δ (1H, s); 7.65 δ (1H, t, J=7.2 Hz); 7.75 δ (1H, t, J=7.9 Hz); 8.1 δ (1H, d, J=8.4 Hz); 8.61 d (1H, d, J=6.2 Hz).

FAB-MS: 438 (M+1)

EXAMPLE 11

7-(Methyl)thio camptothecin

20-Acetoxy-7-methylthio camptothecin (100 mg, 0.23 mmols) was dissolved in reagent grade methanol (20 mL) and added aqueous potassium carbonate (25 mg in 0.1 mL water) and stirred for about 3 hours at low temperature. The resulting reaction mixture was acidified with 1N HCl to precipitate the lactone form of the compound. The precipitated product was then filtered, washed with water (10 mL×4) and with ether (10 mL), dried under vacuum. The pale yellow powder was then analyzed to the desired product (65 mg; 77%).

$^1$H NMR (300 MHz; CDCl$_3$): 0.87 δ (3H, t, J=5.4 Hz); 2.28 δ (2H, q, J=7.2 Hz); 2.31 δ (3H, s); 3.6 δ (1H, s); 5.42 δ (2H, ABq, J$^1$=17.5 Hz; J$^2$=6.1 Hz); 5.61 δ (2H, s); 7.07 δ (1H, s); 7.65 δ (1H, t, J=7.2 Hz); 7.75 δ (1H, t, J=7.9 Hz); 8.1 δ (1H, d, J=8.4 Hz); 8.61 δ (1H, d, J=6.2 Hz)

FAB-MS: 394 (M+1)

EXAMPLE 12

20-Acetoxy-7-methylsulfinyl camptothecin

20- Acetoxy-7-methylthio camptothecin (25 mg, 0.057 mmol) was dissolved in anhydrous methylene chloride (10 mL) and cooled to 0° C. using an ice bath under a stream of argon. Then added freshly purified m-chloroperbenzoic acid (10.3 mg, 1 equivalent) and stirred the reaction mixture for 2 hours at low temperature. The reaction mixture was then diluted with methylene chloride (20 mL) and washed with water (10 mL×4), dried and concentrated to obtain the title compound in the crude form. The product was then flash chromatographed over a bed of florisil using 10% methanol in chloroform to furnish the desired sulfoxide as a diastereomeric mixture in 60% yield.

$^1$H NMR (300 MHz; CDCl$_3$): 0.87 δ (3H, t, J=5.4 Hz); 2.29 δ (2H, q, J=7.2 Hz); 2.31 δ (3H, s); 3.32 δ (3H, s); 5.42 δ (2H, ABq, J$^1$=17.5 Hz; J$^2$6.1 Hz); 5.61 δ (2H, m); 7.07 δ (1H, s); 7.65 δ (1H, t, J=7.2 Hz); 7.75 δ (1H, t, J=7.9 Hz); 8.1 δ (1H, d, J=8.4 Hz); 8.61 δ (1H, d, J=6.2 Hz)

FAB-MS: 454 (M+1)

EXAMPLE 13

7-Methylsulfinyl camptothecin

20-Acetoxy-7-methylsulfinyl camptothecin (100 mg, 0.18 mmols) was dissolved in reagent grade methanol (20 mL) and added aqueous potassium carbonate (25 mg in 0.1 mL water) and stirred for about 3 hours at low temperature. The resulting reaction mixture was acidified with 1N HCl to precipitate the lactone form of the compound. The precipitated product was then filtered, washed with water (10 mL×4) and with ether (10 mL), and dried under vacuum. The pale yellow powder was then analyzed to the desired product (65 mg; 61%).

$^1$H NMR (300 MHz; CDCl$_3$): 0.87 δ (3H, t, J=5.4 Hz); 2.21 δ (2H, q, J=7.2 Hz); 3.6 δ (1H, s); 5.42 δ (2H, ABq, J$^1$=17.5 Hz; J$^2$= 6.1 Hz); 5.61 δ (2H, m); 7.07 δ (1H, s); 7.65 δ (1H, t, J=7.2 Hz); 7.75 δ (1H, t, J=7.9 Hz); 8.1 δ (1H, d, J=8.4 Hz); 8.61 δ (1H, d, J=6.2 Hz)

FAB-MS: 411 (M+1)

EXAMPLE 14

20-Acetoxy-7-ethylthio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mL) and slowly added ethanethiol (0.4 mL) and then stirred the reaction mixture under a balloon pressure for 15 hours in a well ventilated hood. After 15 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.

$^1$H NMR (300 MHz; CDCl$_3$): 0.87 δ (3H, t, J=5.4 Hz); 1.26 δ (3H, t, J=5.8 Hz); 2.21 δ (2H, q, J=7.2 Hz); 2.31 δ (3H, s); 2.28 δ (3H, s); 3.19 δ (2H, q, J=7.2 Hz); 3.6 δ (1H, s); 5.42 δ (2H, ABq, J$^1$=17.5 Hz; J$^2$=6.1 Hz); 5.61 δ (2H, m); 7.07d (1H, s); 7.65 δ (1H, t, J=7.2 Hz); 7.75 δ (1H, t, J=7.9 Hz); 8.1 δ (1H, d, J=8.4 Hz); 8.58 δ (1H, d, J=6.2 Hz)

FAB-MS: 468 (M+1)

EXAMPLE 15

7-(Ethyl)thio camptothecin

20-Acetoxy-7-ethylthio camptothecin (100 mg, 0.21 mmols) was dissolved in reagent grade methanol (20 mL) and added aqueous potassium carbonate (25 mg in 0.1 mL water) and stirred for about 3 hours at low temperature. The resulting reaction mixture was acidified with 1N HCl to precipitate the lactone form of the compound. The precipitated product was then filtered, washed with water (10 mL×4) and with ether (10 mL), dried under vacuum. The pale yellow powder was then analyzed to the desired product (69 mg; 76%).

$^1$H NMR (300 MHz; CDCl$_3$): 0.87 δ (3H, t, J=5.4 Hz); 1.26 δ (3H, t, J=5.8 Hz); 2.21 δ (2H, q, J=7.2 Hz); 2.28 δ (3H, s); 3.19 d (2H, q, J=7.2 Hz); 3.6 d (1H, s); 5.42 δ (2H, ABq, J$^1$=17.5 Hz; J$^2$=6.1 Hz); 5.61 δ (2H, m); 7.07 δ (1H, s); 7.65 δ (1H, t, J=7.2 Hz); 7.75 δ (1H, t, J=7.9 Hz); 8.1 δ (1H, d, J=8.4 Hz); 8.58 δ (1H, d, J=6.2 Hz)

FAB-MS: 425 (M+1)

EXAMPLE 16

20-Acetoxy-7-(isopropyl)thio camptothecin

The intermediate triflate (100 mg, 0.186 mmol) was dissolved in anhydrous 1, 4-dioxane and cooled to 0° C. under a stream of argon. To it was then added diisopropyl ethylamine (0.1 mL; 0.557 mL) and slowly added isopropylthiol (1 mL) and then stirred the reaction mixture under a balloon pressure for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 60.5% yield.

$^1$H NMR (300 MHz; CDCl$_3$): 0.87 δ (3H, t, J=5.4 Hz); 1.26 δ (6H, d, J=5.8 Hz); 2.19 δ (2H, q, J=7.2 Hz); 2.31 δ

(3H, s); 2.28 d (3H, s); 3.59 δ (2H, q, J=7.2 Hz); 5.42 δ (2H, ABq, J¹=17.5 Hz; J²=6.1 Hz); 5.61 δ (2H, m); 7.07 δ (1H, s); 7.65 δ (1H, t, J=7.2 Hz); 7.75 δ (1H, t, J=7.9 Hz); 8.1 δ (1H, d, J=8.4 Hz); 8.58 δ (1H, d, J=6.2 Hz)

FAB-MS: 482 (M+1)

EXAMPLE 17

20-Acetoxy-7-(phenyl)thio camptothecin

The intermediate triflate (100 mg, 0.186 mmol) was dissolved in anhydrous 1, 4-dioxane and cooled to 0° C. under a stream of argon. To it was then added diisopropyl ethylamine (0.1 mL; 0.557 mL) and slowly added phenyl mercaptan (0.2 mL) and then stirred the reaction mixture under a balloon pressure for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.

$^1$H NMR (300 MHz; CDCl$_3$): 0.87 δ (3H, t, J=5.4 Hz); 2.19 δ (2H, q, J=7.2 Hz); 2.28 δ (3H, s); 4.82 δ (2H, ABq, J¹=17.5 Hz; J²=6.1 Hz); 5.61 δ (2H, s); 6.93–7.61 δ (5H, m); 7.07 δ (1H, s); 7.65 δ (1H, t, J=7.2 Hz); 7.75 δ (1H, t, J=7.9 Hz); 8.1 δ (1H, d, J=8.4 Hz); 8.61 δ (1H, d, J=6.2 Hz)

$^{13}$C NMR: δ 7.32, 20.56, 31.63, 50.08, 66.91, 66.98, 75.43, 95.97, 120.47, 125.46, 127.14, 127.49, 128.5, 128.55, 128.72, 129.07, 129.92, 130.15, 130.99, 131.12, 131.56, 140.19, 145.76, 146.11, 149.23, 152.03, 157.07, 167.59, and 169.94

FAB-MS (M+1): 500

EXAMPLE 18

7-(Phenyl)thio camptothecin

20-Acetoxy-7-phenylthio camptothecin (100 mg, 0.21 mmols) was dissolved in reagent grade methanol (20 mL) and added aqueous potassium carbonate (25 mg in 0.1 mL water) and stirred for about 3 hours at low temperature. The resulting reaction mixture was acidified with 1N HCl to precipitate the lactone form of the compound. The precipitated product was then filtered, washed with water (10 mL×4) and with ether (10 mL), dried under vacuum. The pale yellow powder was then analyzed to the desired product (79 mg; 80%).

$^1$H NMR (300 MHz; CDCl$_3$): 0.87 δ (3H, t, J=5.4 Hz); 1.89 δ (2H, q, J=7.2 Hz); 3.6 δ (1H, s); 4.82 δ (2H, ABq, J¹=17.5 Hz; J²=6.1 Hz); 5.61 δ (2H, s); 6.93–7.61 δ (5H, m); 7.07 δ (1H, s); 7.65 δ (1H, t, J=7.2 Hz); 7.75 δ (1H, t, J=7.9 Hz); 8.1 δ (1H, d, J=8.4 Hz); 8.61 δ (1H, d, J=6.2 Hz)

$^{13}$C NMR: δ 7.32, 20.56, 31.63, 50.08, 66.91, 66.98, 75.43, 95.97, 120.47, 125.46, 127.14, 127.49, 128.5, 128.55, 128.72, 129.07, 129.92, 130.15, 130.99, 131.12, 131.56, 140.19, 145.76, 146.11, 149.23, 152.03, 157.07, 167.59, and 169.94

FAB-MS (M+1): 457

EXAMPLE 19

20-Acetoxy-7-(4-fluorophenyl)thio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mL) and slowly added 4-fluorophenyl mercaptan (0.2 mL) and then stirred the reaction mixture under a balloon pressure for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 80.5% yield.

$^1$H NMR (300 MHz; CDCl$_3$): 0.87 δ (3H, t, J=5.4 Hz); 2.19 δ (2H, q, J=7.2 Hz); 2.28 δ (3H, s); 4.82 δ (2H, ABq, J¹=17.5 Hz; J²=6.1 Hz); 5.61 δ (2H, m); 6.93–7.61 δ (4H, m); 7.07 δ (1H, s); 7.65 δ (1H, t, J=7.2 Hz); 7.75 δ (1H, t, J=7.9 Hz); 8.1 δ (1H, d, J=8.4 Hz); 8.61 δ (1H, d, J=6.2 Hz)

$^{13}$C NMR: δ 7.42, 31.63, 50.08, 66.01, 66.98, 72.49, 98.01, 116.92, 117.21, 118.84, 125.12, 128.38, 128.52, 130.43, 130.84, 131.48, 133.19, 133.3, 139.69, 146.17, 149.36, 149.36, 149.98, 152.07, 160.99 and 173.82

FAB-MS (M+1): 518

EXAMPLE 20

7-(4-fluorophenyl)thio camptothecin

20-Acetoxy-7-(4-fluorophenyl)thio camptothecin (100 mg, 0.21 mmols) was dissolved in reagent grade methanol (20 mL) and added aqueous potassium carbonate (25 mg in 0.1 mL water) and stirred for about 3 hours at low temperature. The resulting reaction mixture was acidified with 1N HCl to precipitate the lactone form of the compound. The precipitated product was then filtered, washed with water (10 mL×4) and with ether (10 mL), dried under vacuum. The pale yellow powder was then analyzed to the desired product (79 mg; 80 %)

$^1$H NMR (300 MHz; CDCl$_3$): 0.87 δ (3H, t, J=5.4 Hz); 2.23 δ (2H, q, J=7.2 Hz); 3.6 δ (1H, s); 4.82 δ (2H, ABq, J¹=17.5 Hz; J²=6.1 Hz); 5.61 δ (2H, s); 6.93–7.61 δ (4H, m); 7.07 δ (1H, s); 7.65 δ (1H, t, J=7.2 Hz); 7.75 δ (1H, t, J=7.9 Hz); 8.1 δ (1H, d, J=8.4 Hz); 8.61 δ (1H, d, J=6.2 Hz)

$^{13}$C NMR: δ 7.42, 31.63, 50.08, 66.01, 66.98, 72.49, 98.01, 116.92, 117.21, 118.84, 125.12, 128.38, 128.52, 130.43, 130.84, 131.48, 133.19, 133.3, 139.69, 146.17, 149.36, 149.36, 149.98, 152.07, 160.99 and 173.82

FAB-MS (M+1): 475

EXAMPLE 21

20-Acetoxy-7-trimethylsilyl camptothecin

Hexamethyl disilane (62 μL, 0.3 mmol) was taken up in a flame dried round bottom flask under argon and to it was added anhydrous hexamethyl phosphoramide (0.5 mL) and anhydrous tetrahydrofuran at room temperature. The reaction medium was then cooled to 0° C. using an ice bath and introduced methyllithium (220 μL, estimated as 30.8 mg per mL). The dark colored solution was then stirred at low temperature for 20 to 30 minutes. Copper(I) iodide 42 mg, 0.22 mmol) was taken up in a separate predried round bottom flask and added anhydrous tetrahydrofuran (4 mL) to form a suspension of the copper iodide.

To this suspension was then added tri-n-butyl phosphine (117 μL, 0.47 mmol) and stirred at room temperature for one hour. The resulting homogenous colorless solution was then cooled to 0° C. and transferred to the above organolithium reagent prepared using a cannula at −78° C. The reaction medium was then stirred for the next 15 to 20 minutes. The ongoing intermediate triflate synthon (114 mg, 0.213 mmol) was taken up in anhydrous tetrahydrofuran under a blanket of purified argon and transferred to the above cuprate reagent at −78° C. The resulting dark reaction solution was then stirred for 15 hours and then quenched with saturated ammonium chloride solution. The organic soluble portion was then taken up in chloroform (25 mL). The aqueous portion was then repeatedly extracted with chloroform (25 mL×3). The combined organic portion was then dried over with anhydrous sodium sulfate, filtered and concentrated to yield the desired product in the crude form. The crude form was then flash chromatographed over a bed of silica gel using 10% methanol in chloroform to obtain the title compound in 75% yield.

$^1$H NMR (300 MHz; CDCl$_3$): 0.645 δ (9H, s); 0.90 δ (3H, t, J=5.4 Hz); 2.12 δ (2H, q, J=7.2 Hz); 2.21 δ (3H, s); 2.23 δ ( 3H, s); 5.42 δ (2H, ABq, J$^1$=17.5 Hz; J$^2$=6.1 Hz); 5.49 δ (2H, q, J=2.5 Hz); 7.12 δ (1H, s); 7.87 δ (1H, t, J=7.2 Hz); 7.95 δ (1H, t, J=7.9 Hz); 8.21 δ (1H, d, J=5.4 Hz); 8.27 δ (1H, d, J=5.2 Hz)

$^{13}$C NMR: δ 1.03, 7.58, 30.23, 51.7, 65.23, 72.36, 96.43, 96.43, 118.88, 127.51, 128.31, 128.70, 129.69, 130.48, 131.44, 135.95, 143.46, 145.42, 147.20, 150.15, 156.74, 172.58

FAB-MS: 464 (M+1)

EXAMPLE 22

7-trimethylsilyl camptothecin

20-Acetoxy-7-trimethylsilyl camptothecin (100 mg, 0.21 mmols) was dissolved in reagent grade methanol (20 mL) and added aqueous potassium carbonate (25 mg in 0.1 mL water) and stirred for about 3 hours at room temperature. The resulting reaction mixture is then cooled to 5° C. and acidified with 1N HCl to precipitate the lactone form of the compound. The precipitated product was then filtered, washed with water (10 mL×4) and with ether (10 mL), and dried under vacuum. The pale yellow powder was then analyzed to the desired product (60 mg; 63%).

$^1$H NMR (300 MHz; CDCl$_3$): 0.645 δ (9H, s); 0.90 δ (3H, t, J=5.4 Hz); 2.12 δ (2H, q, J=7.2 Hz); 2.23 δ ( 3H, s); 3.6 δ (1H, S); 5.42 δ (2H, ABq, J$^1$=17.5 Hz; J$^2$=6.1 Hz); 5.49 δ (2H, q, J=2.5 Hz); 7.12 δ (1H, s); 7.87 δ (1H, t, J=7.2 Hz); 7.95 δ (1H, t, J=7.9 Hz); 8.21 δ (1H, d, J=5.4 Hz); 8.27 δ (1H, d, J=5.2 Hz)

$^{13}$C NMR: δ 1.03, 7.58, 30.23, 51.7, 65.23, 72.36, 96.43, 96.43, 118.88, 127.51, 128.31, 128.70, 129.69, 130.48, 131.44, 135.95, 143.46, 145.42, 147.20, 150.15, 156.74, 172.58

FAB-MS: 421 (M+1)

EXAMPLE 23

20-Acetoxy-7-(β-trimethylsilyl)ethynyl camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol) followed by tri(2-furyl) phosphine (20 mg, 0.074 mmol). The resulting solution was stirred for approximately 30 minutes at room temperature. Then added acetylenic trimethylsilane (0.1 mL). The reaction mixture was then stirred at room temperature for 48 hours. The resulting dark brown colored reaction mixture was then diluted with methylene chloride (25 mL), filtered, washed with water (15 mL). The crude product obtained after concentration is then flashed through a columnar bed of florisil, the fractions pooled, concentrated, dried under vacuum and analyzed.

$^1$H NMR (300 MHz; CDCl$_3$): 0.45 δ (9H, s); 0.87 δ (3H, t, J=5.4 Hz); 1.85 δ (2H, q, J=7.2 Hz); 2.31 δ (3H, s); 5.42 δ (2H, ABq, J$^1$=17.5 Hz; J$^2$6.1 Hz); 5.61 δ (2H, m); 7.07 δ (1H, s); 7.87 δ (1H, t, J=7.2 Hz); 7.95 δ (1H, t, J=7.9 Hz); 8.21 δ (1H, d, J=8.4 Hz); 8.27 δ (1H, d, J=6.2 Hz)

FAB-MS (M+1): 501

EXAMPLE 24

20-Acetoxy-7-ethynyl camptothecin

20-Acetoxy-7-trimethylsilyl camptothecin (100 mg, 0.21 mmols) was dissolved in reagent grade methanol (20 mL) and added aqueous potassium carbonate (25 mg in 0.1 mL water) and stirred for about 15 minutes at low temperature. The resulting reaction mixture was then cooled to 5° C. and acidified with 1N HCl to precipitate the lactone form of the compound. The precipitated product was then filtered, washed with water (10 mL×4) and with ether (10 mL), dried under vacuum. The pale yellow powder was then analyzed to the desired product (40 mg; 53%).

$^1$H NMR (300 MHz; CDCl$_3$) 0.90 δ (3H, t, J=5.4 Hz); 2.12 δ (2H, q, J=7.2 Hz); 2.23 δ (3H, s); 3.6 δ (1H, s); 4.06 δ (1H, s); 5.42 d (2H, ABq, J$^1$=17.5 Hz; J$^2$=6.1 Hz); 5.49 δ (2H, q, J=2.5 Hz); 7.12 δ (1H, s); 7.87 δ (1H, t, J=7.2 Hz); 7.95 δ (1H, t, J=7.9 Hz); 8.21 δ (1H, d, J=5.4 Hz); 8.47 δ (1H, d, J=5.2 Hz)

EXAMPLE 25

7-Ethynyl camptothecin

20-Acetoxy-7-Ethynyl camptothecin (50 mg, 0.11 mmols) was dissolved in reagent grade methanol (5 mL) and added aqueous potassium carbonate (25 mg in 0.1 mL water) and stirred for about 2 hours at low temperature. The resulting reaction mixture was then cooled to 5° C. and acidified with 1N HCl to precipitate the lactone form of the compound. The precipitated product was then filtered, washed with water (10 mL×4) and with ether (10 mL), dried under vacuum. The pale yellow powder was then analyzed to the desired product (60 mg; 63%).

$^1$H NMR (300 MHz; CDCl$_3$) 0.90 δ (3H, t, J=5.4 Hz); 2.12 δ (2H, q, J=7.2 Hz); 3.6 δ (1H, s); 4.06 δ (1H, s); 5.42 δ (2H, ABq, J$^1$=17.5 Hz; J$^2$=6.1 Hz); 5.49 δ (2H, q, J=2.5 Hz); 7.12 δ (1H, s); 7.87 δ (1H, t, J=7.2 Hz); 7.95 δ (1H, t, J=7.9 Hz); 8.21 δ (1H, d, J=5.4 Hz); 8.47 δ (1H, d, J=5.2 Hz)

EXAMPLE 26

7-(β-trimethylsilyl)ethyl camptothecin

Camptothecin (500 mg, 1.44 mmols) was suspended in deionized water (10 mL) and freshly distilled 3-trimethylsilyl-1-propanal (3.0 mL; excess) followed by dropwise addition of concentrated sulfuric acid (5.5 mL) at 0° C. using an ice bath over a period of 15 min. To the above stirred reaction medium was then introduced 30% aqueous solution of hydrogen peroxide (2 mL) followed by iron sulfate heptahydrate (156 mg) in 1 mL water. The reaction mixture was then stirred at 25° C. for an additional 24 hours. The reaction mixture was then diluted with ice-cold water and extracted with chloroform (50 mL×3). The combined organic portion was then dried over anhydrous sodium sulfate, filtered and concentrated to obtain the crude product in 65% yield. The crude product was then purified over a silica gel column using 90% chloroform-methanol mixture to furnish 0.46 gm of the title compound (54% yield).

$^1$H NMR (300 MHz; CDCl$_3$): 0.01 δ (9H, s); 0.48 δ (2H, q, J=4.8 Hz); 0.90 δ (3H, t, J=5.4 Hz); 1.53 δ (2H, q, J=6.6

Hz); 2.12 δ (2H, q, J=7.2 Hz); 2.23 δ (3H, s); 3.6 d (1H, s); 5.42 δ (2H, ABq, $J^1$=17.5 Hz; $J^2$=6.1 Hz); 5.49 δ (2H, q, J=2.5 Hz); 7.12 δ (1H, s); 7.87 δ (1H, t, J=7.2 Hz); 7.95 δ (1H, t, J=7.9 Hz); 8.21 δ (1H, d, J=5.4 Hz); 8.27 δ (1H, d, J=5.2 Hz)

$^{13}$C NMR: δ 1.03, 7.58, 9.62, 23.48, 30.23, 51.7, 65.23, 72.36, 96.43, 96.43, 118.88, 127.51, 128.31, 128.70, 129.69, 130.48, 131.44, 135.95, 143.46, 145.42, 147.20, 150.15, 156.74, 172.58

FAB-MS: 492 (M+1)

EXAMPLE 27

20-Acetoxy-7-(β-trimethylsilyl)ethylthio camptothecin

The intermediate triflate (100 mg, 0.186 mmol) was dissolved in anhydrous 1,4-dioxane and cooled to 0° C. under a stream of argon. To it was then added diisopropyl ethylamine (0.1 mL; 0.557 mL) and slowly added trimethylsilyl ethanethiol (0.25 mL) and then stirred the reaction mixture under a balloon pressure of argon for 15 hours in a well ventilated hood. After 15 hours, the reaction mixture was diluted with methylene chloride (25 mL) and washed with water (20 mL×4), dried over anhydrous sodium sulfate, filtered and concentrated to obtain the crude product of the title compound in approximately 80% yield.

$^1$H NMR (300 MHz; CDCl$_3$): 0.01 δ (9H, s); 0.87 δ (3H, t, J=5.4 Hz); 0.98 δ (2H, q, J=4.8 Hz); 1.26 δ (3H, t, J=5.8 Hz); 1.89 δ (2H, q, J=7.2 Hz); 2.31 δ (3H, s); 2.28 d (3H, s); 3.05 δ (2H, q, J=5 Hz); 3.19 δ (2H, q, J=7.2 Hz); 5.42 δ (2H, ABq, $J^1$=17.5 Hz; $J^2$=6.1 Hz); 5.61 δ (2H, s); 7.07 δ (1H, s); 7.65 δ (1H, t, J=7.2 Hz); 7.75 δ (1H, t, J=7.9 Hz); 8.1 δ (1H, d, J=8.4 Hz); 8.58 δ (1H, d, J=6.2 Hz)

FAB-MS: 523 (M+1)

EXAMPLE 28

7-(β-Trimethylsilyl)ethylthio camptothecin

20-Acetoxy-7-ethylthio camptothecin (100 mg, 0.21 mmols) was dissolved in reagent grade methanol (20 mL) and added aqueous potassium carbonate (25 mg in 0.1 mL water) and stirred for about 3 hours at low temperature. The resulting reaction mixture was acidified with 1N HCl to precipitate the lactone form of the compound. The precipitated product was then filtered, washed with water (10 mL×4) and with ether (10 mL) and dried under vacuum. The pale yellow powder was then analyzed to the desired product (69 mg; 76%).

$^1$H NMR (300 MHz; CDCl$_3$): 0.01 δ (9H, s); 0.87 δ (3H, t, J=5.4 Hz); 0.98 δ (2H, q, J=4.8 Hz); 1.26 δ (3H, t, J=5.8 Hz); 1.89 δ (2H, q, J=7.2 Hz); 2.31 δ (3H, s); 2.28 δ (3H, s); 3.05 δ (2H, q, J=5 Hz); 3.19 δ (2H, q, J=7.2 Hz); 3.6 δ (1H, s); 5.42 δ (2H, ABq, $J^1$=17.5 Hz; $J^2$=6.1 Hz); 5.61 δ (2H, s); 7.07 δ (1H, s); 7.65 δ (1H, t, J=7.2 Hz); 7.75 δ (1H, t, J=7.9 Hz); 8.1 δ (1H, d, J=8.4 Hz); 8.58 δ (1H, d, J=6.2 Hz)

FAB-MS: 481 (M+1)

EXAMPLE 29

20-Acetoxy-7-(α-trimethylsilyl)methylthio camptothecin

The intermediate triflate (100 mg, 0.186 mmol) was dissolved in anhydrous 1,4-dioxane (2 mL) and cooled to 0° C. under a stream of argon. To it was then added diisopropyl ethylamine (0.1 mL; 0.557 mL) and slowly added trimethylsilyl methanethiol (0.2 mL) and then stirred the reaction mixture under a balloon pressure of argon for 15 hours in a well ventilated hood. After 48 hours, the reaction mixture was diluted with methylene chloride (25 mL) and washed with water (20 mL×4), dried over anhydrous sodium sulfate, filtered and concentrated to obtain the crude product of the title compound in approximately 70% yield.

$^1$H NMR (300 MHz; CDCl$_3$): 0.15 δ (9H, s); 0.87 δ (3H, t, J=5.4 Hz); 1.26 δ (3H, t, J=5.8 Hz); 2.21 δ (3H, s); 2.19 δ (2H, q, J=7.2 Hz); 2.31 δ (2H, s); 2.38 δ (2H, s); 5.42 δ (2H, ABq, $J^1$=17.5 Hz; $J^2$=6.1 Hz); 5.61 δ (2H, s); 7.07 δ (1H, s); 7.65 d (1H, t, J=7.2 Hz); 7.75 d (1H, t, J=7.9 Hz); 8.22 δ (1H, d, J=8.4 Hz); 8.55 δ (1H, d, J=6.2 Hz)

FAB-MS: 509 (M+1)

EXAMPLE 30

7-(α-Trimethylsilyl)methylthio camptothecin

20-Acetoxy-7-methylthio camptothecin (100 mg, 0.21 mmols) is dissolved in reagent grade methanol (20 mL) and added aqueous potassium carbonate (25 mg in 0.1 mL water) and stirred for about 3 hours at low temperature. The resulting reaction mixture was acidified with 1N HCl to precipitate the lactone form of the compound. The precipitated product was then filtered, washed with water (10 mL×4) and with ether (10 mL), dried under vacuum. The pale yellow powder was then analyzed to the desired product (59 mg; 67%).

$^1$H NMR (300 MHZ; CDCl$_3$) 0.15 δ (9H, s); 0.87 δ (3H, t, J=5.4 Hz); 1.26 δ (3H, t, J=5.8 Hz); 2.19 δ (2H, q, J=7.2 Hz); 2.28 δ (2H, S); 2.38 δ (2H, s); 3.6 δ (1H, s); 5.42 δ (2H, ABq, $J^1$=17.5 Hz; $J^2$=6.1 Hz); 5.61 δ (2H, s); 7.07 δ (1H, s); 7.65 δ (1H, t, J=7.2 Hz); 7.75 δ (1H, t, J=7.9 Hz); 8.1 δ (1H, d, J=8.4 Hz); 8.58 δ (1H, d, J=6.2 Hz)

FAB-MS: 467 (M+1)

EXAMPLE 31

20-Deoxy camptothecin

Camptothecin (500 mg, 1.44 mmol) was suspended in 1,4-dioxane (10 mL) and added Lawsson's reagent (290.5 mg, 0.72 mmol). The reaction mixture was then heated to 90° C. for 10 hours under an inert atmosphere. The resultant homogeneous reaction mixture was then concentrated, organic portion was taken up in chloroform (25 mL) and the aqueous fraction was repeatedly extracted with chloroform (25 mL×3). The combined organic portion was then concentrated to get the title compound in the crude form. The crude product was then flash chromatographed over a bed of florisil using 10% chloroform in methanol to furnish the desired product in 40% yield in diastereomeric mixture.

$^1$H NMR (300 MHz; CDCl$_3$) 1.07 δ (3H, t, J=5.4 Hz); 2.12 δ (2H, q, J=7.2 Hz); 3.69 δ (1H, t, J=6.6 Hz); 5.42 δ (2H, ABq, $J^1$=17.5 Hz; $J^2$=6.1 Hz); 5.59 δ (2H, q, J=2.5 Hz); 7.62 δ (1H, s); 7.71 δ (1H, t, J=7.2 Hz); 7.85 δ (1H, t, J=7.9 Hz); 8.01 δ (1H, d, J=5.4 Hz); 8.23 δ (1H, d, J=5.2 Hz); 8.47 δ (1H, s)

$^{13}$C NMR: δ 11.1, 25.25, 29.6, 45.81, 49.93, 66.04, 99.76, 120.79, 128.10, 128.24, 128.72, 129.8, 130.73, 131.2, 146.12, 147.27, 149.06, 158.01 and 171.01

FAB (M+1): 361.2

EXAMPLE 32

20-Methanesulfonyl camptothecin

To a suspension of camptothecin (2.0 g, 5.7 mmol) in 100 mL dichloromethane was added 20 mL pyridine, and 6.5 mL methanesulfonyl chloride. The mixture was stirred at room temperature under nitrogen for 3 days. It turned to homogeneous solution. Solvents were removed by high vacuum. The residue was purified by flash column chromatography, eluted with ethyl acetate. 1.135 g 20-mesylcamptothecin was obtained, 46% yield.

$^1$H NMR (CDCl$_3$) δ 8.38 (1H, s), 8.23 (1H, d, J=8.7 Hz), 7.91 (1H, d, J=8.1 Hz), 7.82 (1H, t, J=8.4 Hz), 7.66 (1H, t, J=7.8 Hz), 7.62 (1H, s), 5.64 (1H, d, J=17.7 Hz), 5.36 (1H, d, J=17.7 Hz), 5.29 (2H, s), 3.32 (3H, s), 2.29 (2H, m), 0.97 (3H, t, J=7.5 Hz).

EXAMPLE 33

20-Deoxycamptothecin

To a solution of 20-mesylcamptothecin (0.59 g, 1.38 mmol) in 30 dioxane was added 0.30 g of sodium iodide and tributylstannyl hydride (0.90 mL, 2.5 equiv.). The mixture was heated to reflux for 4 hours. After cooling down to room temperature, the reaction mixture was diluted with 50 mL diethyl ether. The precipitate was filtered off. The mother liquor was then diluted with 50 mL of hexane. Precipitate was then combined with collected residue and dissolved in chloroform, washed with brine, dried over anhydrous sodium sulfate. The solvent was removed to provide 0.386 g of 20-deoxycamptothecin, 69% yield.

$^1$H NMR (CDCl$_3$) δ 8.39 (1H, s), 8.22 (1H, d, J=8.7 Hz), 7.91 (1H, d, J=8.1 Hz), 7.83 (1H, t, J 8.4 Hz), 7.66 (1H, t, J=7.8 Hz), 7.18 (1H, s), 5.64 (1H, d, J=16.5 Hz), 5.36 (1H, d, J=16.5 Hz), 5.29 (2H, s), 3.62 (1H, t, J=6.6 Hz), 2.09 (2H, m), 1.09 (3H, t, J=7.5 Hz).

EXAMPLE 34

20-Acetoxy-7-(γ-trimethylsilyl) (α-propenyl camptothecin

The 20-acetoxy-7-triflate (100 mg, 0.1855 mmol) was dissolved anhydrous and degassed anhydrous dimethylformamide (5 mL) and added zinc chloride (50.5 mg, 0.371 mmol). To it was then added tris(dibenzylideneacetonyl)bis palladium(0) (17 mg, 0.371 mmol) followed by tri(2-furyl) phosphine (20 mg, 0.074 mmol). The resulting solution was stirred for approximately 30 minutes at room temperature. Then added propen-α-yl trimethylsilane (0.1 mL). The reaction mixture was then stirred at room temperature for 48 hours. The resulting dark brown colored reaction mixture was then diluted with methylene chloride (25 ml), filtered, washed with water (15 ml). The crude product obtained after concentration was then flashed through a columnar bed of florisil, the fractions pooled, concentrated, dried under vacuum and analyzed.

$^1$H NMR (300 MHz; CDCl$_3$) 0.26 6 (9H, s); 0.97 δ (3H, t, J=5.4 Hz); 2.02 δ (2H, s); 2.24 δ (2H, q, J=7.2 Hz); 2.21 δ (3H, s); 5.42 δ (2H, ABq, J$^1$=17.5 Hz; J$^2$=6.1 Hz); 5.61 δ (2H, m); 7.2 δ (1H, s); 7.77 δ (1H, t, J=7.2 Hz); 7.85 δ (1H, t, J=7.9 Hz); 8.21 δ (1H, d, J=8.4 Hz); 8.32 δ (1H, d, J=6.2 Hz)

FAB-MS (M+1): 501

EXAMPLE 35

20-Acetoxy-7-(α-Propenyl) camptothecin

20-Acetoxy-7-(γ-trimethylsilyl) propen-α-yl camptothecin (100 mg, 0.21 mmols) was dissolved in reagent grade methanol (20 mL) and added aqueous potassium carbonate (25 mg in 0.1 mL water) and stirred for about 15 minutes at low temperature. The resulting reaction mixture was then cooled to 5° C. and acidified with 1N HCl to precipitate the lactone form of the compound. The precipitated product was then filtered, washed with water (10 mL×4) and with ether (10 mL), dried under vacuum. The pale yellow powder was then analyzed to the desired product (40 mg; 53%).

$^1$H NMR (300 MHz; CDCl$_3$): 0.97 δ (3H, t, J=5.4 Hz); 2.02 δ (2H, s); 2.24 δ (2H, q, J=7.2 Hz); 2.21 δ (3H, s); 5.42 δ (2H, ABq, J$^1$=17.5 Hz; J$^2$=6.1 Hz); 5.61 δ (2H, m); 7.2 δ (1H, s); 7.77 δ (1H, t, J=7.2 Hz); 7.85 δ (1H, t, J=7.9 Hz); 8.21 δ (1H, d, J=8.4 Hz); 8.32 δ (1H, d, J=6.2 Hz)

EXAMPLE 36

7-(γ-trimethylsilyl) α-propenyl camptothecin

20-Acetoxy-7-(γ-trimethylsilyl) α-propenyl camptothecin (50 mg, 0.11 mmols) was dissolved in reagent grade methanol (5 mL) and added aqueous potassium carbonate (25 mg in 0.1 mL water) and stirred for about 2 hours at low temperature. The resulting reaction mixture was then cooled to 5° C. and acidified with 1N HCl to precipitate the lactone form of the compound. The precipitated product was then filtered, washed with water (10 mL×4) and with ether (10 mL), dried under vacuum. The pale yellow powder was then analyzed as the desired product (60 mg; 63%) and 10% of the isomerized congener the corresponding 7-allenic derivative.

$^1$H NMR (300 MHz; CDCl$_3$) 0.26 δ (9H, s); 0.97 δ (3H, t, J=5.4 Hz); 2.02 δ (2H, s, corresponds to the acetylenic counterpart); 2.24 δ (2H, q, J=7.2 Hz); 5.42 δ (2H, ABq, J$^1$=17.5 Hz; J$^2$=6.1 Hz); 5.61 δ (2H, m); 7.2 δ (1H, s); 7.77 δ (1H, t, J=7.2 Hz); 7.85 δ (1H, t, J=7.9 Hz); 8.21 δ (1H, d, J=8.4 Hz); 8.32 δ (1H, d, J=6.2 Hz)

EXAMPLE 37

7-Ethyl-20-dehydroxy camptothecin

7-Ethyl camptothecin (456 mg, 1.213 mmol) was suspended in 1,4-dioxane (10 mL) and added Lawsson's reagent (245.26 mg, 0.665 mmol). The reaction mixture was then heated to 90° C. for 10 hours under an inert atmosphere. The resultant homogeneous reaction mixture was then concentrated, the organic portion was taken up in chloroform (25 mL) and the aqueous fraction was repeatedly extracted with chloroform (25 mL×3). The combined organic portion was then concentrated to get the title compound in the crude form. The crude product was then flash chromatographed over a bed of florisil using 10% chloroform in methanol to furnish the desired product in 40% yield in diastereomric mixture.

$^1$H NMR (300 MHz; CDCl$_3$): 1.08 δ (3H, t, J=5.4 Hz); 2.38 δ (3H, t, J=5.4 Hz; 2.1 δ (2H, q, J=7.2 Hz); 3.19 δ (2H, q, J=7.8 Hz); 3.69 δ (1H, t, J=6.6 Hz); 5.42 δ (2H, ABq, J$^1$=17.5 Hz; J$^2$=6.1 Hz); 5.59 δ (2H, q, J=2.5 Hz); 7.62 δ (1H, s); 7.71 δ (1H, t, J=7.2 Hz); 7.85 δ (1H, t, J=7.9 Hz); 8.12 δ (1H, d, J=5.4 Hz); 8.20 δ (1H, d, J=5.2 Hz)

$^{13}$C NMR: δ 11.13, 13.87, 22.91, 25.25, 45.75, 49.20, 65.97, 99.56, 120.45, 123.52, 126.85, 127.02, 130.12, 130.6, 145.79, 146.76, 147.25, 149.97, 151.95, 157.97, 171.01

FAB (M+1): 389.1

EXAMPLE 38

7-(β-trimethylsilyl)ethyl-20-deoxy camptothecin

20-Deoxy camptothecin (200 mg) is suspended in 10 mL of water and to it was added ferrous sulfate heptahydrate (400 mg) followed by glacial acetic acid (5 mL). The above reaction mixture was stirred for 15 minutes and then added concentrated sulfuric acid (4 mL) dropwise maintaining the reaction temperature around 15° C. Finally 30% hydrogen peroxide (0.2 ml) was added to the above reaction mixture and stirred at room temperature for 3 hours. The organic portion was then taken up in chloroform. The aqueous portion is then repeatedly extracted with chloroform (50 mL×5). The combined organic fraction was then washed with water, brine and then dried over anhydrous sodium sulfate. The product containing portion was then filtered and evaporated to obtain 120 mg of the desired product in the crude form. The crude product was then chromatographed over silica gel using ethyl acetate-chloroform mixture to furnish the title compound (85 mg).

$^1$H NMR (CDCl$_3$) δ 8.39δ (1H, s), 8.22δ (1H, d, J=8.7 Hz), 7.91δ (1H, d, J=8.1 Hz), 7.83δ (1H, t, J=8.4 Hz), 7.66δ (1H, t, J=7.8 Hz), 7.18δ (1H, s), 5.64δ (1H, d, J=16.5 Hz), 5.36δ (1H, d, J=16.5 Hz), 5.29δ (2H, s), 3.62δ (1H, t, J=6.6 Hz), 2.09δ (2H, m), 1.09δ (3H, t, J=7.5 Hz) and 0.12δ (9H, s).

The foregoing description has been directed to particular embodiments of the invention in accordance with requirements of the Patent Statutes for the purposes of illustration and explanation. It will be apparent, however, to those skilled in this art, that many modifications, changes and variations in the claimed antitumor compositions, solutions, methods of administration of the antitumor compositions set forth will be possible without departing from the scope and spirit of the claimed invention. It is intended that the following claims be interpreted to embrace all such modifications and changes.

What is claimed is:

1. A compound having the formula:

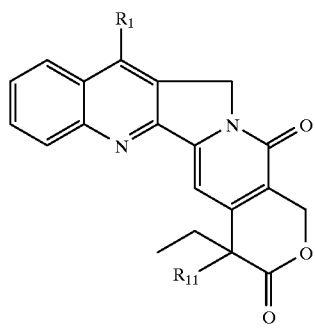

(I)

wherein R$_1$ is (C$_0$–C$_6$ alkylene, C$_2$–C$_8$ alkenylene, or C$_2$–C$_8$ alkynylene)—SiR$_8$,R$_9$,R$_{10}$; or —X—(C$_1$–C$_6$ alkylene, C$_2$–C$_8$ alkenylene, or C$_2$–C$_8$ alkynylene)—SiR$_8$,R$_9$, R$_{10}$.

R$_8$, R$_9$ and R$_{10}$ are each individually hydrogen or lower alkyl;

R$_{11}$ is hydrogen, hydroxy, acyloxy or alkoxy; and

X is sulfur.

2. The compound of claim 1 wherein R$_1$ is -(C$_0$–C$_6$ alkylene, C$_2$–C$_8$ alkenylene, or C$_2$–C$_8$ alkynylene)—Si(CH$_3$)$_3$; or —S—(C$_0$–C$_6$ alkylene, C$_2$–C$_8$ alkenylene, or C$_2$–C$_8$ alkynylene )—Si(CH$_3$)$_3$.

3. The compound of claim 1 wherein R$_{11}$ is hydrogen.

4. The compound of claim 1 wherein R$_1$ is —X—lower alkyl—Si(CH$_3$)$_3$.

5. The compound of claim 4 wherein X is sulfur.

6. The compound of claim 4 wherein X is absent.

7. The pharmaceutically acceptable salts of the compound of claim 1.

8. The compound of claim 1 wherein R$_1$ is trimethylsilyl ethyl.

9. The compound of claim 1 wherein R$_1$ is trimethylsilyl ethynyl.

10. A pharmaceutical formulation comprising the compound of claim 1, and one or more pharmaceutically acceptable excipients, carriers or diluents.

11. A method of treating patients with cancer susceptible of treatment with camptothecin comprising administering an effective amount of a compound of claim 1 to a patient in need of treatment for cancer.

12. A pharmaceutical formulation comprising the compound of claim 7, and one or more pharmaceutically acceptable excipients, carriers or diluents.

13. A pharmaceutical formulation comprising the compound of claim 8, and one or more pharmaceutically acceptable excipients, carriers or diluents.

14. A pharmaceutical formulation comprising the compound of claim 9, and one or more pharmaceutically acceptable excipients, carriers or diluents.

* * * * *

UNITED STATES PATENT AND TRADEMARK OFFICE
CERTIFICATE OF CORRECTION

PATENT NO. : 5,910,491  
DATED : June 8, 1999  
INVENTOR(S) : Frederick H. Hausheer, et al.

Page 1 of 1

It is certified that error appears in the above-identified patent and that said Letters Patent is hereby corrected as shown below:

<u>Column 29,</u>
Line 10, delete "492", and substitute therefore -- 450 --.

Signed and Sealed this

Second Day of October, 2001

Attest:

NICHOLAS P. GODICI
Attesting Officer    *Acting Director of the United States Patent and Trademark Office*

UNITED STATES PATENT AND TRADEMARK OFFICE
CERTIFICATE OF CORRECTION

PATENT NO. : 5,910,491
DATED : June 8, 1999
INVENTOR(S) : Frederick H. Hausheer et al.

It is certified that error appears in the above-identified patent and that said Letters Patent is hereby corrected as shown below:

Column 19,
Line 53, change "(2H, s)" to -- (1H, s) --.

Column 20,
Lines 19 and 45, change "(2H, s)" to -- (1H, s) --.
Line 44, delete "2.78 δ (3H, s)".

Column 22,
Line 20, delete the second occurrence of "3.6δ (1H, s)".

Column 24,
Line 25, delete "2.28 δ (3H, s)".
Lines 45-46, delete "2.28 δ (3H, s)".

Column 25,
Line 1, delete "2.28 d (3H, s)".

Column 27,
Lines 9-10 and 35, delete "2.23 δ (3H, s)".

Column 29,
Line 1, delete "2.23 δ (3H, s)".
Lines 29-30 and 52-53, delete "1.26 δ (3H, t, J=5.8 Hz)".
Lines 30 and 53, delete "2.31 δ (3H, s)".
Lines 31 and 54, delete "3.19 δ (2H, q, J=7.2 Hz)".

Column 30,
Lines 9 and 30, delete "1.26 δ (3H, t, J=5.8 Hz)".
Line 9, delete "2.21 δ (3H, s)".
Lines 10 and 31, delete "2.38 δ (2H, s)".

UNITED STATES PATENT AND TRADEMARK OFFICE
CERTIFICATE OF CORRECTION

PATENT NO. : 5,910,491
DATED : June 8, 1999
INVENTOR(S) : Frederick H. Hausheer et al.

It is certified that error appears in the above-identified patent and that said Letters Patent is hereby corrected as shown below:

Column 32,
Line 34, delete "dehydroxy" and substitute therefor -- deoxy --.

Signed and Sealed this

Ninth Day of September, 2003

JAMES E. ROGAN
*Director of the United States Patent and Trademark Office*